US005380830A

United States Patent [19]

Gonda

[11] Patent Number: 5,380,830

[45] Date of Patent: Jan. 10, 1995

[54] MOLECULAR CLONES OF BOVINE IMMUNODEFICIENCY-LIKE VIRUS

[75] Inventor: Matthew A. Gonda, Walkersville, Md.

[73] Assignee: The United States of America as represented by the Secretary of the Department of Health and Human Services, Washington, D.C.

[21] Appl. No.: 980,324

[22] Filed: Nov. 24, 1992

Related U.S. Application Data

[63] Continuation of Ser. No. 408,815, Sep. 18, 1989, abandoned.

[51] Int. Cl.[6] .......................... C07H 21/04; C12N 7/00; C12N 7/02; C12N 15/49

[52] U.S. Cl. .......................... 536/23.1; 435/235.1; 435/236; 435/320.1; 536/23.72; 935/6; 935/9; 935/19; 935/32

[58] Field of Search .................. 435/235.1, 236, 320.1; 536/23.1, 23.72; 935/6, 9, 19, 32

[56] References Cited

PUBLICATIONS

Braun, M. J. et al (1988) Virology 167, 515–523.
Gonda, M. A. et al (1987) Nature 330, 388–391.
Wain-Hobson, S. et al (1985) Cell 40, 9–17.
A. Adachi et al (1986) J. Virology 59:284–291.
G. M. Shaw et al (1984) Science 226:1165–1171.

*Primary Examiner*—Jacqueline Stone
*Assistant Examiner*—Johnny F. Railey, II
*Attorney, Agent, or Firm*—Susan S. Rucker

[57] ABSTRACT

Biologically active proviral molecular clones of bovine immunodeficiency-like virus and cell lines infected with the same have been prepared. Various utilities of the clones are described.

3 Claims, 28 Drawing Sheets

FIG. 6A

```
       ↦R                                          A
1      TTCAGCTCGTGTAGCTCATTACGTCCGAGCTCCCCAACCTACAGCCTGAGAGGCACTGGCTCGGTTGGGTAGCCA  75

                           ▨          R.↔ U5
76     GCCTTTCGGGTAATAAAGGCTTGTTGGCATTCGGCATCTACCCGTGCCTCCTGTCTTGTCTTACTCGAGCGAACC  150

              G                                           U5 ↤  tRNA Lys 1,2 binding site
151    CACAACTCCGTCCTGCTGAGCTCACAGCTCGCGGGGCGGTGAAGAACACCCAACAGT[TGGCGCCCAACGTGGGG]C  225

                                                                      ↓sd
226    TCGAGTAAGAGAGACTCGGCTCGAGTAAAAGAAGACCCAGCTCGAACGAGAAGACTCCGGACAGGTGAGTAGTTG  300

                          A                                         T
301    CGTGTTTTCCCCGGGATGAAGAGAAGGGAGTTAGAAAAGAAGCTTCGTAAGGTTAGGGTGACACCCCAACAGGAT  375
          start gag →  M  K  R  R  E  L  E  K  K  L  R  K  V  R  V  T  P  Q  Q  D

376    AAATATTATACTATAGGGAATCTTCAATGGGCCATTAGAATGATAAATCTAATGGGGATCAAATGTGTGTGTGAC  450
       K  Y  Y  T  I  G  N  L  Q  W  A  I  R  M  I  N  L  M  G  I  K  C  V  C  D

451    GAGGAGTGCTCGGCAGCAGAGGTAGCCCTTATCATAACCCAATTTTCAGCTTTAGACTTAGAAAATTCTCCTATC  525
       E  E  C  S  A  A  E  V  A  L  I  I  T  Q  F  S  A  L  D  L  E  N  S  P  I

526    AGAGGTAAGGAGGAGGTGGCCATAAAAAATACTCTGAAGGTTTTCTGGTCCCTGCTGGCGGGGTACAAACCAGAG  600
       R  G  K  E  E  V  A  I  K  N  T  L  K  V  F  W  S  L  L  A  G  Y  K  P  E

                                                                       A
601    AGTACAGAAACGGCCCTAGGATATTGGGAGGCCTTTACATATAGAGAAAGGGAGGCCAGAGCTGATAAGGAAGGC  675
       S  T  E  T  A  L  G  Y  W  E  A  F  T  Y  R  E  R  E  A  R  A  D  K  E  G
```

FIG. 6B

```
676  GAAATTAAGAGTATTTACCCTTCCCTAACACAGAACACACAGAATAAGAAGCAGACATCGAATCAGACAAACACT  750
     E  I  K  S  I  Y  P  S  L  T  Q  N  T  Q  N  K  K  Q  T  S  N  Q  T  N  T

751  CAATCATTACCAGCTATCACTACTCAAGATGGTACTCCTAGGTTTGATCCTGACCTCATGAAGCAGCTTAAGATC  825
     Q  S  L  P  A  I  T  T  Q  D  G  T  P  R  F  D  P  D  L  M  K  Q  L  K  I

826  TGGTCAGACGCCACTGAAAGAAATGGGGTTGACCTTCATGCAGTGAATATATTAGGGGTCATTACAGCAAACCTA  900
     W  S  D  A  T  E  R  N  G  V  D  L  H  A  V  N  I  L  G  V  I  T  A  N  L

901  GTACAGGAAGAAATTAAACTCCTCTTGAATAGTACACCCAAGTGGAGATTAGATGTACAACTTATAGAATCAAAA  975
     V  Q  E  E  I  K  L  L  L  N  S  T  P  K  W  R  L  D  V  Q  L  I  E  S  K

976  GTAAGAGAGAAAGAAAATGCCCACAGAACGTGGAAACAGCATCATCCAGAAGCCCCAAAAACAGATGAAATCATC  1050
     V  R  E  K  E  N  A  H  R  T  W  K  Q  H  H  P  E  A  P  K  T  D  E  I  I

1051 GGTAAGGGGCTTAGTTCTGCTGAACAAGCCACCCTGATCTCAGTAGAATGCAGAGAAACTTTCAGACAGTGGGTG  1125
     G  K  G  L  S  S  A  E  Q  A  T  L  I  S  V  E  C  R  E  T  F  R  Q  W  V

                                                        A
1126 CTGCAGGCAGCTATGGAGGTGGCACAGGCAAAACATGCTACCCCAGGTCCCATCAACATTCATCAGGGACCCAAG  1200
     L  Q  A  A  M  E  V  A  Q  A  K  H  A  T  P  G  P  I  N  I  H  Q  G  P  K

1201 GAGCCGTACACAGACTTTATAAATAGATTAGTGGCAGCCCTTGAAGGTATGGCGGCTCCAGAAACCACAAAAGAA  1275
     E  P  Y  T  D  F  I  N  R  L  V  A  A  L  E  G  M  A  A  P  E  T  T  K  E
```

FIG. 6C

```
                                                                        C         T
1276  TACTTACTCCAACATCTATCTATTGATCATGCCAATGAAGACTGCCAGTCTATTCTAAGACCTTTGGGACCCAAC  1350
      Y  L  L  Q  H  L  S  I  D  H  A  N  E  D  C  Q  S  I  L  R  P  L  G  P  N

                                                     C
1351  ACCCCAATGGAGAAAAAATTAGAAGCATGTAGGGTAGTGGGATCTCAGAAATCAAAGATGCAATTTTTGGTAGCA  1425
      T  P  M  E  K  K  L  E  A  C  R  V  V  G  S  Q  K  S  K  M  Q  F  L  V  A

1426  GCTATGAAAGAAATGGGGATCCAATCACCAATTCCAGCAGTCTTGCCTCACACACCAGAAGCATATGCCTCCCAA  1500
      A  M  K  E  M  G  I  Q  S  P  I  P  A  V  L  P  H  T  P  E  A  Y  A  S  Q

1501  ACCTCAGGGCCCGAGGATGGTAGGAGATGTTACGGATGTGGGAAGACAGGACATTTGAAGAGGAATTGTAAACAG  1575
      T  S  G  P  E  D  G  R  R  C  Y  G  C  G  K  T  G  H  L  K  R  N  C  K  Q

1576  CAAAAATGCTACCATTGTGGCAAACCTGGCCACCAAGCAAGAAACTGCAGGTCAAAAAACGGGAAGTGCTCCTCT  1650
      Q  K  C  Y  H  C  G  K  P  G  H  Q  A  R  N  C  R  S  K  N  G  K  C  S  S
start pol → M  L  P  L  W  Q  T  W  P  P  S  K  K  L  Q  V  K  K  R  E  V  L  L  C

1651  GCCCCTTATGGGCAGAGGAGCCAACCACAGAACAATTTTCACCAGAGCAACATGAGTTCTGTGACCCCATCTGCA  1725
      A  P  Y  G  Q  R  S  Q  P  Q  N  N  F  H  Q  S  N  M  S  S  V  T  P  S  A
        P  L  W  A  E  E  P  T  T  E  Q  F  S  P  E  Q  H  E  F  C  D  P  I  C  T

1726  CCCCCTCTTATATTAGATTAGACAAACAGCCTTTTATAAAGGTGTTCATAGGGGGAAGATGGGTAAAAGGGTTAG  1800
      P  P  L  I  L  D  * end gag
        P  S  Y  I  R  L  D  K  Q  P  F  I  K  V  F  I  G  G  R  W  V  K  G  L  V
```

FIG. 6D

```
1801 TAGACACTGGAGCAGATGAGGTAGTGCTTAAGAACATACATTGGGATAGGATAAAAGGGTATCCAGGGACACCAA 1875
      D  T  G  A  D  E  V  V  L  K  N  I  H  W  D  R  I  K  G  Y  P  G  T  P  I

1876 TTAAACAAATTGGGGTAAATGGAGTAAATGTGGCCAAAAGGAAGACCCACGTAGAGTGGAGATTTAAGGATAAGA 1950
      K  Q  I  G  V  N  G  V  N  V  A  K  R  K  T  H  V  E  W  R  F  K  D  K  T

1951 CTGGGATAATTGATGTCTTGTTCTCAGATACTCCTGTAAACCTTTTTGGGAGATCTCTTCTACGTAGCATAGTGA 2025
      G  I  I  D  V  L  F  S  D  T  P  V  N  L  F  G  R  S  L  L  R  S  I  V  T

             A
2026 CTTGCTTCACCCTACTTGTTCACACAGAAAAAATCGAACCCCTACCCGTCAAGGTAAGGGGACCAGGGCCTAAGG 2100
      C  F  T  L  L  V  H  T  E  K  I  E  P  L  P  V  K  V  R  G  P  G  P  K  V

2101 TACCCCAGTGGCCCTTGACAAAAGAAAAGTATCAGGCTCTTAAGGAAATTGTGAAAGATCTTTTAGCAGAAGGAA 2175
      P  Q  W  P  L  T  K  E  K  Y  Q  A  L  K  E  I  V  K  D  L  L  A  E  G  K

2176 AAATTTCCGAAGCTGCTTGGGATAACCCATATAATACCCCAGTTTTTGTTATAAAGAAAAAGGGAACGGGAAGAT 2250
      I  S  E  A  A  W  D  N  P  Y  N  T  P  V  F  V  I  K  K  K  G  T  G  R  W

2251 GGAGGATGCTAATGGATTTTAGGGAATTAAATAAGATAACAGTTAAAGGACAAGAATTCTCTACAGGCTTACCTT 2325
      R  M  L  M  D  F  R  E  L  N  K  I  T  V  K  G  Q  E  F  S  T  G  L  P  Y

                                                                    C
2326 ACCCTCCAGGAATTAAGGAATGTGAACACTTAACTGCAATAGATATAAAAGATGCCTACTTTACTATCCCTTTAC 2400
      P  P  G  I  K  E  C  E  H  L  T  A  I  D  I  K  D  A  Y  F  T  I  P  L  H
```

FIG. 6E

```
2401  ATGAGGACTTTAGACCCTTTACAGCCTTCTCTGTAGTCCCTGTAAATCGAGAAGGACCTATAGAGAGGTTCCAGT  2475
        E  D  F  R  P  F  T  A  F  S  V  V  P  V  N  R  E  G  P  I  E  R  F  Q  W

2476  GGAATGTTCTACCACAAGGATGGGTATGTAGCCCTGCCATTTATCAGACTACCACCCAGAAGATTATAGAAAACA  2550
        N  V  L  P  Q  G  W  V  C  S  P  A  I  Y  Q  T  T  T  Q  K  I  I  E  N  I

2551  TTAAAAAGAGTCACCCAGATGTCATGTTGTATCAATATATGGATGATTTGTTGATTGGGTCTAATAGGGATGATC  2625
        K  K  S  H  P  D  V  M  L  Y  Q  Y  M  D  D  L  L  I  G  S  N  R  D  D  H

2626  ATAAGCAAATAGTGCAGGAAATCAGGGATAAGTTAGGATCATATGGTTTCAAGACTCCAGATGAAAAGGTCCAGG  2700
        K  Q  I  V  Q  E  I  R  D  K  L  G  S  Y  G  F  K  T  P  D  E  K  V  Q  E

2701  AAGAGAGAGTGAAATGGATCGGTTTTGAGCTCACACCCAAGAAATGGCGTTTTCAGCCCAGGCAACTAAAGATAA  2775
        E  R  V  K  W  I  G  F  E  L  T  P  K  K  W  R  F  Q  P  R  Q  L  K  I  K

2776  AAAACCCACTCACAGTAAATGAATTACAGCAATTAGTAGGTAATTGTGTTTGGGTACAGCCAGAAGTAAAAATCC  2850
        N  P  L  T  V  N  E  L  Q  Q  L  V  G  N  C  V  W  V  Q  P  E  V  K  I  P

2851  CTCTATACCCCTTAACCGATCTACTGAGGGATAAGACCAATCTCCAAGAAAAGATACAACTAACACCAGAAGCCA  2925
        L  Y  P  L  T  D  L  L  R  D  K  T  N  L  Q  E  K  I  Q  L  T  P  E  A  I

2926  TCAAGTGTGTAGAAGAATTCAATCTAAAACTAAAAGATCCAGAATGGAAAGATAGAATAAGAGAAGGAGCAGAAT  3000
        K  C  V  E  E  F  N  L  K  L  K  D  P  E  W  K  D  R  I  R  E  G  A  E  L
```

FIG. 6F

```
3001  TAGTCATAAAAATACAGATGGTTCCTCGGGGCATAGTATTTGATCTGTTGCAAGATGGAAATCCCATATGGGGAG  3075
       V  I  K  I  Q  M  V  P  R  G  I  V  F  D  L  L  Q  D  G  N  P  I  W  G  G

                                                                          A
3076  GAGTAAAAGGACTAAATTATGATCATTCAAACAAAATAAAAAAGATACTTAGAACTATGAATGAGCTGAACAGAA  3150
       V  K  G  L  N  Y  D  H  S  N  K  I  K  K  I  L  R  T  M  N  E  L  N  R  T

3151  CAGTGGTAATTATGACAGGAAGAGAAGCTAGTTTCCTGCTTCCTGGGTCTTCTGAAGATTGGGAAGCGGCACTCC  3225
       V  V  I  M  T  G  R  E  A  S  F  L  L  P  G  S  S  E  D  W  E  A  A  L  Q

3226  AGAAGGAAGAAAGTCTAACACAAATATTCCCAGTAAAGTTTTATAGGCACTCCTGCAGATGGACCTCCATATGTG  3300
       K  E  E  S  L  T  Q  I  F  P  V  K  F  Y  R  H  S  C  R  W  T  S  I  C  G

          T
3301  GGCCAGTAAGAGAAAATCTAACCACCTACTATACTGACGGAGGGAAGAAAGGGAAAACAGCTGCAGCAGTATATT  3375
       P  V  R  E  N  L  T  T  Y  Y  T  D  G  G  K  K  G  K  T  A  A  A  V  Y  W

3376  GGTGTGAAGGAAGGACTAAGTCAAAGGTATTTCCAGGAACCAATCAACAGGCGGAATTGAAGGCCATATGCATGG  3450
       C  E  G  R  T  K  S  K  V  F  P  G  T  N  Q  Q  A  E  L  K  A  I  C  M  A

3451  CTCTCTTGGATGGACCACCAAAAATGAATATCATAACAGATAGTAGATACGCCTATGAGGGAATGAGAGAAGAAC  3525
       L  L  D  G  P  P  K  M  N  I  I  T  D  S  R  Y  A  Y  E  G  M  R  E  E  P

3526  CAGAAACGTGGGCCAGGGAAGGAATCTGGCTGGAGATTGCCAAGATATTGCCCTTTAAGCAGTACGTGGGGGTCG  3600
       E  T  W  A  R  E  G  I  W  L  E  I  A  K  I  L  P  F  K  Q  Y  V  G  V  G
```

FIG. 6G

```
                 .         .         .         .         .         .         .
3601    GGTGGGTGCCTGCACATAAAGGGATAGGAGGAAATACAGAGGCAGATGAAGGAGTTAAGAAAGCCTTAGAACAGA    3675
         W  V  P  A  H  K  G  I  G  G  N  T  E  A  D  E  G  V  K  K  A  L  E  Q  M

             .         .         .         .         .         .         .         .
3676    TGGCCCCGTGTAGCCCTCCTGAGGCCATTCTATTAAAACCAGGAGAAAAACAAAATCTGGAGACAGGGATCTACA    3750
         A  P  C  S  P  P  E  A  I  L  L  K  P  G  E  K  Q  N  L  E  T  G  I  Y  M

                 .         .         .         .         .         .         .
3751    TGCAGGGGCTTAGACCACAAAGCTTCCTCCCAAGAGCAGACTTACCAGTAGCCATCACAGGAACCATGGTAGATT    3825
         Q  G  L  R  P  Q  S  F  L  P  R  A  D  L  P  V  A  I  T  G  T  M  V  D  S

             .         .         .         .         .         .         .         .
3826    CAGAGCTACAGCTACAGCTACTTAACATAGGAACTGAGCATATAAGAATCCAAAAAGATGAGGTCTTCATGACCT    3900
         E  L  Q  L  Q  L  L  N  I  G  T  E  H  I  R  I  Q  K  D  E  V  F  M  T  C

                 .         .         .         .         .         .         .
3901    GTTTCCTAGAAAATATCCCCTCAGCCACTGAAGATCATGAGAGATGGCATACCTCACCAGACATTTTGGTTAGGC    3975
         F  L  E  N  I  P  S  A  T  E  D  H  E  R  W  H  T  S  P  D  I  L  V  R  Q

             .      G.G        .         .         .        .C         .  G      .
3976    AGTTCCATCTCCCTAAGAGAATAGCTAAAGAGATAGTAGCCAGATGCCAAGAATGTAAAAGGACAACCACTAGCC    4050
         F  H  L  P  K  R  I  A  K  E  I  V  A  R  C  Q  E  C  K  R  T  T  T  S  P

                 .         .         .         .         .         .         .
4051    CAGTCAGAGGAACAAACCCCAGAGGTCGATTCTTATGGCAGATGGACAATACTCACTGGAATAAAACAATTATTT    4125
         V  R  G  T  N  P  R  G  R  F  L  W  Q  M  D  N  T  H  W  N  K  T  I  I  W

             .         .         .         .         .         .         .         .
4126    GGGTAGCAGTAGAGACAAATTCAGGATTAGTGGAAGCTCAGGTGATCCCTGAAGAAACAGCACTACAAGTAGCTC    4200
         V  A  V  E  T  N  S  G  L  V  E  A  Q  V  I  P  E  E  T  A  L  Q  V  A  L
```

FIG. 6H

```
4201 TCTGCATTTTACAGCTAATCCAGAGATATACAGTTCTTCACTTACATAGTGACAACGGGCCGTGCTTTACTGCAC 4275
      C  I  L  Q  L  I  Q  R  Y  T  V  L  H  L  H  S  D  N  G  P  C  F  T  A  H

4276 ACAGGATAGAAAATCTATGTAAGTATCTGGGGATCACAAAAACTACGGGAATACCCTACAACCCACAATCCCAGG 4350
      R  I  E  N  L  C  K  Y  L  G  I  T  K  T  T  G  I  P  Y  N  P  Q  S  Q  G

4351 GAGTTGTAGAAAGAGCCCACAGAGATCTAAAAGACAGATTGGCAGCTTATCAGGGAGATTGTGAAACCGTAGAAG 4425
      V  V  E  R  A  H  R  D  L  K  D  R  L  A  A  Y  Q  G  D  C  E  T  V  E  A

4426 CAGCCCTTAGCCTCGCATTAGTTTCTTTAAATAAAAAAAGAGGGGGAATAGGGGGCCATACACCATATGAAATAT 4500
      A  L  S  L  A  L  V  S  L  N  K  K  R  G  G  I  G  G  H  T  P  Y  E  I  Y

4501 ACCTAGAATCAGAACATACCAAATACCAAGACCAACTAGAACAACAATTTTCAAAACAAAAAATTGAAAAGTGGT 4575
      L  E  S  E  H  T  K  Y  Q  D  Q  L  E  Q  Q  F  S  K  Q  K  I  E  K  W  C

4576 GTTACGTAAGGAACAGAAGAAAGGAATGGAAAGGACCCTACAAAGTGTTGTGGGACGGAGACGGGGCAGCAGTAA 4650
                      start vif →  M  E  R  T  L  Q  S  V  V  G  R  R  R  G  S  S  N
      Y  V  R  N  R  R  K  E  W  K  G  P  Y  K  V  L  W  D  G  D  G  A  A  V  I

                                                                       ↓sa
4651 TAGAGGAAGAGGGAAAAACAGCCTTATATCCACACCGTCATATGCGCTTCATCCCCCCCCCAGATTCAGATATCC 4725
     R  G  R  G  K  N  S  L  I  S  T  P  S  Y  A  L  H  P  P  P  R  F  R  Y  P
      E  E  E  G  K  T  A  L  Y  P  H  R  H  M  R  F  I  P  P  P  D  S  D  I  Q
```

FIG. 6I

```
4726 AAGATGGGAGTTCGTGAGGCAGACAGAATACAGCATGACCGCGTGCGTAAGAAAAGGGAAATTAGTCCTTACTTA 4800
start W→M G V R E A D R I Q H D R V R K K R E I S P Y L
 R W E F V R Q T E Y S M T A C V R K G K L V L T Y
 D G S S * end pol

                                                   A
4801 CCAGTACGCGATCTGGAAAAGAGTCTGGACGATAGAAACAGGATTTACAGATCCAAGTCTGTTTATGACCCCAGC 4875
 P V R D L E K S L D D R N R I Y R S K S V Y D P S
 Q Y A I W K R V W T I E T G F T D P S L F M T P A

4876 TGGAACACACACCACTGAAGAAATAGGTCACTTAGATCTCTTTTGGCTTAGGTACTGTTCATGTCCGCATGAGAT 4950
 W N T H H * end W
 G T H T T E E I G H L D L F W L R Y C S C P H E M

4951 GCCCCCGTGGCTAGACTTCCTTAGAGGCACCCTCAATCTACGCATTTCCTGTCGACGCGCTCTTCAAGCGTCAGT 5025
 P P W L D F L R G T L N L R I S C R R A L Q A S V

 A.                    ↓sa
5026 GTTGACTAGCACCCCTAGACACTCCCTCCAACGCTTAGCTGCACTTCAGCTGTGCACTAACGCATGTCTCTGTTG 5100
                                              start Y→M S L L
 L T S T P R H S L Q R L A A L Q L C T N A C L C W

                                                  ↓sa
5101 GTACCCGTTAGGACGCATCAACGACACCACCCCGTTGTGGTTGAACTTTTCGTCTGGGAAGGAACCAACGATCCA 5175
 V P V R T H Q R H H P V V V E L F V W E G T N D P
 Y P L G R I N D T T P L W L N F S S G K E P T I Q
```

FIG. 6J

```
5176  ACAACTGAGTGGCCACCCCTAACTCGTCGTAACATTCATAGATTGTGGCAATATGCCCGGACCTTGGGTGGCGAT  5250
       T  T  E  W  P  P  L  T  R  R  N  I  H  R  L  W  Q  Y  A  R  T  L  G  G  D
        Q  L  S  G  H  P  *end vif        start tat exon 1 → M  P  G  P  W  V  A  M

5251  GATAATGTTGCCACAGCCCAAAGAAAGCTTTGGAGGAAAGCCAATTGGCTGGCTTTTGTGGAACACGTGCAAAGG  5325
       D  N  V  A  T  A  Q  R  K  L  W  R  K  A  N  W  L  A  F  L  E  H  V  Q  R
        I  M  L  P  Q  P  K  E  S  F  G  G  K  P  I  G  W  L  F  W  N  T  C  K  G

                                                                          ↓sa
5326  ACCTAGGCGGGACTGTCCACATTGTTGTTGTCCCATATGTAGTTGGCATTGTCAGCTTTGCTTTTTGCAGAAAAA  5400
       T  *end Y
        P  R  R  D  C  P  H  C  C  C  P  I  C  S  W  H  C  Q  L  C  F  L  Q  K  N
              G                                               ↓sd
5401  TCTAGGAATCAACTATGGATCAGGACCTAGACCGCGCGGAACGCGGGGAAAGGGGAGGAGGATCCGAAGAACTGC  5475
        L  G  I  N  Y  G  S  G  P  R  P  P  R  G  T  R  G  K  G  R  R  I  R  R  T  A
           start env → M  D  Q  D  L  D  R  A  E  R  G  E  R  G  G  G  S  E  E  L  L
       start rev exon 1 →

          A
5476  TTCAGGAGGAGATCAACGAAGGGAGGCTGACAGCCAGAGAAGCTTTACAAACATGGATCAATAACGGTGAGATCC  5550
       S  G  G  D  Q  R  R  E  A  D  S  Q  R  S  F  T  N  M  D  Q  *end tat exon 1
        Q  E  E  I  N  E  G  R  L  T  A  R  E  A  L  Q  T  W  I  N  N  G  E  I  H

5551  ACCCTTGGGTCCTGGCAGGAATGCTGTCCATGGGAGTAGGAATGCTACTAGGAGTATATTGTCAGTTACCAGACA  5625
        P  W  V  L  A  G  M  L  S  M  G  V  G  M  L  L  G  V  Y  C  Q  L  P  D  T

                                                               A
5626  CACTGATTTGGATACTAATGTTTCAATTATGCCTTTATTGGGGTTTGGGTGAAACATCTAGAGAATTAGACAAGG  5700
        L  I  W  I  L  M  F  Q  L  C  L  Y  W  G  L  G  E  T  S  R  E  L  D  K  D
```

FIG. 6K

```
                  .         .         .         .         .         .         .
5701 ATAGTTGGCAGTGGGTCAGAAGTGTATTTATAATAGCAATATTGGGAACTCTCACTATGGCAGGAACTGCTTTGG 5775
       S  W  Q  W  V  R  S  V  F  I  I  A  I  L  G  T  L  T  M  A  G  T  A  L  A

         .         .         .         .
5776 CCGACGACGATCAAAGTACTTTAATCCCCAATATCACAAAAATTCCTACAAAGGACACGGAACCCGGTTGCACCT 5850
       D  D  D  Q  S  T  L  I  P  N  I  T  K  I  P  T  K  D  T  E  P  G  C  T  Y

                                                                 .         .
5851 ATCCGTGGATATTAATCCTCTTGATTTTGGCTTTCATACTGGGAATTCTGGGTATAATACTTGTCTTGAGACGCA 5925
       P  W  I  L  I  L  L  I  L  A  F  I  L  G  I  L  G  I  I  L  V  L  R  R  S

         .         .         .         .         .         .         .         .
5926 GCAACTCGGAGGATATATTGGCAGCCAGAGATACCATAGATTGGTGGCTCTCAGCTAATCAGGAAATACCTCCAA 6000
       N  S  E  D  I  L  A  A  R  D  T  I  D  W  W  L  S  A  N  Q  E  I  P  P  K

                  .         .         .         .         .         A         .
6001 AGTTTGCTTTCCCAATAATATTAATATCTTCCCCTCTAGCAGGCATAATAGGATATTATGTCATGGAAAGGCACT 6075
       F  A  F  P  I  I  L  I  S  S  P  L  A  G  I  I  G  Y  Y  V  M  E  R  H  L

         .         .         .         .        CT         .         .         .
6076 TAGAGATCTTCAAAAAGGGATGTCAAATTTGTGGGAGCCTGAGCAGCATGTGGGGAATGCTTTTGGAAGAAATTG 6150
       E  I  F  K  K  G  C  Q  I  C  G  S  L  S  S  M  W  G  M  L  L  E  E  I  G

          C A .         .    G .         . G         .         .         .
6151 GCAGGTGGCTCGCACGTAGGGAATGGAATGTTAGTAGAGTAATGGTTATCCTCTTAATCAGCTTCAGTTGGGGAA 6225
       R  W  L  A  R  R  E  W  N  V  S  R  V  M  V  I  L  L  I  S  F  S  W  G  M

         .   C     .         .         . G       .         .         .         .
6226 TGTATGTCAATAGGGTAAATGCCTCAGGGTCACATGTAGCCATGGTCACCAGCCCTCCAGGGTACCGCATAGTGA 6300
       Y  V  N  R  V  N  A  S  G  S  H  V  A  M  V  T  S  P  P  G  Y  R  I  V  N
```

FIG. 6L

```
                    .         .         .         .         .         .         .
6301  ATGATACCAGCCAGGCACCTTGGTATTGCTTCTCCTCGGCACCAATCCCAACGTGTAGTTCCTCTCAGTGGGGAG  6375
       D  T  S  Q  A  P  W  Y  C  F  S  S  A  P  I  P  T  C  S  S  S  Q  W  G  D

          .         .         .         .         .         .         . C       .
6376  ACAAATATTTTGAGGAGAAAATAAACGAGACACTGGTCAAACAGGTGTATGAACAGGCCGCGAAACATTCGAGAG  6450
       K  Y  F  E  E  K  I  N  E  T  L  V  K  Q  V  Y  E  Q  A  A  K  H  S  R  A

        G   .         . G       .         .         .         .       T .
6451  CCACATGGATTGAACCTGATCTATTGGAGGAAGCAGTCTATGAGCTAGCTCTGTTATCAGCTAATGACAGTCGTC  6525
       T  W  I  E  P  D  L  L  E  E  A  V  Y  E  L  A  L  L  S  A  N  D  S  R  Q

          .         .         .         T         .         .         .         .
6526  AGGTGGTGGTAGAAAATGGTACAGACGTATGTAGCTCACAGAACTCGAGCACAAACAAAGGCCACCCAATGACGC  6600
       V  V  V  E  N  G  T  D  V  C  S  S  Q  N  S  S  T  N  K  G  H  P  M  T  L

                    .         .         .         .         .         .         .
6601  TTCTAAAGTTGAGAGGGCAGGTGTCAGAAACTTGGATAGGGAATTCCTCCCTCCAGTTTTGTGTCCAGTGGCCAT  6675
       L  K  L  R  G  Q  V  S  E  T  W  I  G  N  S  S  L  Q  F  C  V  Q  W  P  Y

          .         .         .         .         .         .         .         .
6676  ATGTCTTGGTAGGTCTTAATAATAGTGATAGTAATATTAGCTTCAATTCGGGAGATTGGATAGCAACCAATTGTA  6750
       V  L  V  G  L  N  N  S  D  S  N  I  S  F  N  S  G  D  W  I  A  T  N  C  M

                    .         .         . G       .         .         .         .
6751  TGCACCCAATTACACTAAATAAAAGTGCACAAGATCTAGGAAAAAATTTTCCGAGACTAACATTTCTTGACGGAC  6825
       H  P  I  T  L  N  K  S  A  Q  D  L  G  K  N  F  P  R  L  T  F  L  D  G  Q

          .         .         .         .         .         .         . C       .
6826  AACTGTCCCAGTTGAAGAACACACTGTGCGGACATAACACAAACTGTTTGAAATTTGGAAACAAGTCCTTCAGTA  6900
       L  S  Q  L  K  N  T  L  C  G  H  N  T  N  C  L  K  F  G  N  K  S  F  S  T
```

FIG. 6M

6901 CAAATTCCCTAATACTATGCCAAGACAACCCCATCGGCAACGACACCTTTTATAGCCTAAGTCATTCCTTCTCAA 6975

N S L I L C Q D N P I G N D T F Y S L S H S F S K

G

6976 AACAGGCCTCTGCCCGGTGGATTCTTGTAAAGGTCCCCAGCTATGGGTTTGTGGTAGTAAATGACACAGATACAC 7050

Q A S A R W I L V K V P S Y G F V V V N D T D T P

7051 CACCATCCCTCCGCATCCGAAAGCCTCGAGCAGTCGGACTAGCAATATTCCTGCTTGTGCTGGCTATCATGGCCA 7125

P S L R I R K P R A V G L A I F L L V L A I M A I

OMP TMP

7126 TCACATCCTCCTTGGTGGCAGCTACAACGCTCGTGAACCAGCACACGACGGCTAAGGTTGTGGAGAGGGTTGTGC 7200

T S S L V A A T T L V N Q H T T A K V V E R V V Q

7201 AAAATGTGTCATATATTGCTCAAACCCAGGACCAATTCACCCACCTGTTCAGGAATATAAACAACAGATTAAATG 7275

N V S Y I A Q T Q D Q F T H L F R N I N N R L N V

G

7276 TCCTACACCATAGAGTTTCATACTTGGAGTATGTAGAGGAAATCAGACAAAAACAAGTATTCTTTGGTTGCAAAC 7350

L H H R V S Y L E Y V E E I R Q K Q V F F G C K P

7351 CTCATGGAAGGTATTGCCACTTTGACTTTGGACCAGAGGAAGTTGGATGGAACAATAGTTGGAATAGCAAAACTT 7425

H G R Y C H F D F G P E E V G W N N S W N S K T W

G.

7426 GGAATGATCTACAAGATGAGTATGATAAGATAGAAGAAAAAATATTAAAAATTCGAGTGGACTGGCTCAATAGCT 7500

```
7501  CCCTGAGTGACACACAGGACACCTTTGGCCTGGAGACCTCTATTTTTGACCATTTAGTGCAATTGTTTGATTGGA  7575
                                                      start rev exon 2 →  L  D
       L  S  D  T  Q  D  T  F  G  L  E  T  S  I  F  D  H  L  V  Q  L  F  D  W  T

                                                                          ↓sa
7576  CTTCTTGGAAAGACTGGATAAAAATCATTATAGTAATCATTGTACTTTGGCTTCTGATAAAGATTCTCCTAGGTA  7650
      F  L  E  R  L  D  K  N  H  Y  S  N  H  C  T  L  A  S  D  K  D  S  P  R  Y
       S  W  K  D  W  I  K  I  I  I  V  I  I  V  L  W  L  L  I  K  I  L  L  G  M

                                              A                             A
7651  TGTTAAGAAGCTGCGCCAAGGTCAGCCAGAATTACCAACATCTCCCGGCGGAGGAGGAGGACGGGGACACAGAGC  7725
tat exon 2 → E  A  A  P  R  S  A  R  I  T  N  I  S  R  R  R  R  R  T  G  T  Q  S
      V  K  K  L  R  Q  G  Q  P  E  L  P  T  S  P  G  G  G  G  G  R  G  H  R  A
       L  R  S  C  A  K  V  S  Q  N  Y  Q  H  L  P  A  E  E  E  D  G  D  T  E  P

7726  CAGAAAGCTCCCCGGCGAGAGGAGACCCGGCTTCTGGAAGTCTCTACGAGAATTGGTTGAACAAAATAGGAGAAA  7800
      Q  K  A  P  R  R  E  E  T  R  L  L  E  V  S  T  R  I  G  * end tat exon 2
      R  K  L  P  G  E  R  R  P  G  F  W  K  S  L  R  E  L  V  E  Q  N  R  R  K
       E  S  S  P  A  R  G  D  P  A  S  G  S  L  Y  E  N  W  L  N  K  I  G  E  S

7801  GCAAGAACGACGCCTATCGGGTCTGGACAGAAGAATACAACAGCTTGAGGATCTTGTTCGCCACATGTCGCTGGG  7875
      Q  E  R  R  L  S  G  L  D  R  R  I  Q  Q  L  E  D  L  V  R  H  M  S  L  G
       K  N  D  A  Y  R  V  W  T  E  E  Y  N  S  L  R  I  L  F  A  T  C  R  W  D

      C
7876  ATCTCCTGACCCCTCAACTCCTTCAGCTTCCGTTCTTTCTGTTAACCCTCCTGCTCAAACTCCTTTGGGACATCT  7950
      S  P  D  P  S  T  P  S  A  S  V  L  S  V  N  P  P  A  Q  T  P  L  G  H  L
       L  L  T  P  Q  L  L  Q  L  P  F  F  L  L  T  L  L  L  K  L  L  W  D  I  F
```

FIG. 6O

```
                    polypurine tract                  ↦ U3
7951  TCCGCCACGCTCCTATTTTAAACTTAAAAGGGTGGACTGTGGGGCAGGGTGGACCTCAGGACAACAGCAGCCCC   8025
       P  P  R  S  Y  F  K  L  K  R  V  D  C  G  A  G  W  D  L  R  T  T  A  A  P
        R  H  A  P  I  L  N  L  K  G  W  T  V  G  Q  G  G  T  S  G  Q  Q  Q  P  P

     NF-κB sequence
8026  CGGACTTCCCATATGTGAATTGGACTGGATCCAGGGAACAAAATAACCCAGAAGGGGGATTAGACTCTGGGGCTT   8100
       G  L  P  I  C  E  L  D  W  I  Q  G  T  K  * end rev exon 2
        D  F  P  Y  V  N  W  T  G  S  R  E  Q  N  N  P  E  G  G  L  D  S  G  A  W

8101  GGTATGAAGGCCTGAGAGGTTCTCAGTAGATTGTAAGTCTTCGGCGAGACTGCATGTCTGCACGTAGACAGGAAA   8175
        Y  E  G  L  R  G  S  Q  * end env

                         core enhancer
8176  TGTTTATCTTCTCAGCTGATTGTGGTTAGGCCGATTACTGGAAACTAGACAACCTGATTCATTAGTGGTTAAGAT   8250

                    CAAT sequence
8251  TATGCATAAGTGCTCGCAATGATGTAGCTGCTTACGCTTGCTTACTCCGCCCTGAAACGCCTACCTTAACACGCA   8325

                       G TATA sequence         U3 ↔ R
8326  ACACGCCCACCTGTAAGAATATATAAACCATATCTTCACTCTGTACTTCAGCTCGTGTAGCTCATTAGCTCCGAG   8400

                      A.                                     poly(A) signal
8401  CTCCCCAACCTACAGCCTGAGAGGCACTGGCTCGGTTGGGTAGCCAGCCTTTCGGGTAATAAAGGCTTGTTGGCA   8475

        R. ↤
8476  TTCGGCA                                                                      8482
```

FIG. 10

| | | | | | | | | | | |
|---|---|---|---|---|---|---|---|---|---|---|
| BIV | N | I | H | Q | G | P | K | E | P | Y |
| HIV-1 | D | I | R | Q | G | P | K | E | P | F |
| HIV-2 | D | I | K | Q | G | P | K | E | P | F |
| $SIV_{mac}$ | D | V | K | Q | G | P | K | E | P | F |
| $SIV_{agm}$ | D | I | R | Q | G | P | K | E | P | F |
| EIAV | N | I | R | Q | G | A | K | E | P | Y |
| Visna | L | V | K | Q | K | N | T | E | S | Y |
| Consensus | B | I | b | Q | G | P | K | E | P | a |

FIG. 12

| | | | | % similarity |
|---|---|---|---|---|
| HIV-1 | aa22 | C T N - C Y C K K C C F H C Q V C F I T K A L G I S Y | 47 | (100) |
| HIV-2 | 50 | C N N S C Y C K R C C Y H C Q M C F L N K G L G I C Y | 75 | (67) |
| $SIV_{mac}$ | 50 | C Y N T C Y C K K C C Y H C Q F C F L K K G L G I S Y | 75 | (74) |
| $SIV_{agm}$ | 26 | C K N K C F C K K C C Y H C Q L C F L Q K G L G V T Y | 52 | (63) |
| BIV127 | 38 | C P H - C C C P I C S W H C Q L C F L Q K N L G I N Y | 63 | (56) |
| EIAV | 1 | - - V L L Q E A R P N Y H C Q L C F L - R S L G I D Y | 25 | (37) |
| Visna | 63 | R R N - C G C R L C N P G W G S - - Q V R N - - V E L | 94 | (19) |
| Consensus | | C p N - C n C K p C C Y H C Q n C F L p K p L G I p Y | | |

MOLECULAR CLONES OF BOVINE IMMUNODEFICIENCY-LIKE VIRUS

This application is a continuation of application Ser. No. 07/408,815 filed Sep. 18, 1991 and now abandoned.

The present invention is generally related to molecular cloning of viruses. More particularly, the present invention is related to producing biologically active proviral molecular clones of the bovine immunodeficiency-like virus (BIV) and applications thereof.

BACKGROUND OF THE INVENTION

A recently characterized virus, designated as BIV, is an infectious lentivirus that causes lymphadenopathy, lymphocytosis, central nervous system lesions, progressive weakness, and emaciation (Van Der Maaten et al, 1972. *J. Natl. Cancer Inst.* 49:1649–1657). Preliminary epidemiologic evidence suggests that BIV infection is widespread in cattle populations in the U.S. BIV has the morphology of a lentivirus, encodes a reverse transcriptase (RT) with a $Mg^{2+}$ cation preference, and has immunologic cross-reactivity with HIV, SIV, and EIAV (Gonda et al, 1987, *Nature* 330:388–391). Moreover, the detection of sequence homology in the highly conserved RT domain of pol conclusively demonstrates that BIV Is a lentivirus, distinct from all previously characterized lentivirus isolates (Gonda et al, supra).

Non-functional clones of BIV have been prepared (Gonda et al, supra). The reasons for lack of biological activity in these clones are not fully understood.

SUMMARY OF THE INVENTION

It is, therefore, an object of the present invention to provide biologically active full-length proviral molecular clones of BIV.

It is a further object of the present invention to provide BIV-infected mammalian cell lines that are a stable source of BIV.

It is a still further object of the present invention to provide BIV-specific antigens, antibodies and DNA useful for the development of vaccines, diagnostic reagents, probes and the like.

It is yet another object of the present invention to provide animals wherein BIV-specific sequences are incorporated into the host through infection or transgenic animal technology for use as models for studying disease and testing anti-viral agents, drugs, vaccines and the like, and for inducing resistance to disease.

Various other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

[Parts A, a, B and b] shows (A) heteroduplex analyses of BIV clones 39 and 56 FIGS. 1A and 1C are actual heteroduplexes; FIGS. 1B and 1D are interpretive drawings. The stringency of hybridization, which was calculated using formulas presented in Gonda (1988), was $T_m-42°$ C. Thin and thick lines in FIGS. 1B and 1D are single- and double-stranded DNA, respectively. The 5' and 3' ends of the inserts are indicated as well as the arms of the cloning vector. The solid arrow in FIG. 1B indicates the position of the deletion/insertion loop. The pol cross-hybridizing regions in FIG. 1D are indicated by the open arrows.

FIG. 2A show an Actual heteroduplex; FIG. 2B shows an interpretive drawing. The calculated stringency of the spreading solution hybridization was $T_m+2$. The 5' and 3' ends of the inserts are indicated as well as the arms of the cloning vector. In FIG. 2B the double-stranded homologous sequences in the insert are shown as thick lines and the single-stranded non-homologous flanking sequences are represented by thin lines.

FIGS . 4B and 4C show microinjection of BIV clones 106 and 127 respectively into bovine embryonic spleen (BESp) cells.

FIG. 5A shows an Immature budding particle. FIG. 5B shows an Immature extracellular particle. FIG. 5C shows an Mature extracellular particle with typical bar- or cone-shaped core.

FIGS. 6A–6D show the complete nucleotide sequences of BIV 106 and 127 in the form predicted for the viral RNA. Translations are provided for the major ORFs which were deduced based on their structural homology and/or analogous location in the genome to those of other lentiviruses. All of the nucleotides for the BIV 127 genome are shown; nucleotides for BIV 106, where they are different or absent from BIV 127, are shown above the BIV 127 sequence; deletions are indicated by the thick solid line. Nucleotide changes that cause a coding substitution in BIV 106 are presented in Table 1. Annotations for the $U_3$, R, and $U_5$ boundaries, start and stop of major structural, catalytic, and nonstructural/regulatory ORFs, potential promoter sequences (TATA and CAT boxes), cap site, polyadenylation signal, polypurine tract, NF-kB consensus sequence, and tRNA binding site, OMP-TMP cleavage site, and splice acceptor (↓SA) and splice donor (↓SD) sites are given.

FIG. 10 shows the alignment of the highly conserved region of lentivirus gag proteins. A global alignment was performed using the PIR Align program with a gap penalty of 6. The region shown represents residues 293–302 of the predicted BIV 127 gag protein sequence (BIV 106 and 127 are identical in this region). Boxed residues are those which are the same as BIV. The consensus line shows residues which are the same in at least five of the seven viruses. Lower case symbols indicate conservation of amino acid character, but not a specific amino acid at that position: B=aspartate or asparagine; a=aromatic; b=basic.

(FIG. 11A) Alignment of a portion of the BIV 127 and HIV-$1_{HXB2}$ TMP using UWGCG Gap (gap weight 2.0, gap length weight 0.2). The transmembrane and $NH_2$-terminal hydrophobic domains of the HIV-1 TMP are indicated below the sequence. Arrows indicate conserved cysteine residues. Potential sites of N-linked glycosylation are boxed. Hydropathy plots of the BIV 127 (FIG. 11B) and HIV-$1_{HXB2}$ (FIG. 11C) TMP using UWGCG Peptidestructure and Plotstructure. Hydrophobic regions appear below the mean; hydrophilic regions appear above the mean.

FIG. 12 shows the alignment of a highly conserved region of the tat (exon 1) ORF of several lentiviruses. The nucleotide sequences of the indicated viruses were obtained from GenBank and the tat region was translated using the program Translate (UWGCG). Each peptide sequence was optimally aligned with the HIV-$1_{HXB2}$ sequence using UWGCG Gap (gap weight 5.0, gap length weight 0.3); percent homology of each sequence with HIV-1 is given. Multiple sequence alignment was generated using Genalign. Lower case symbols are p=polar; n=nonpolar.

DETAILED DESCRIPTION OF THE INVENTION

Figure 1A:
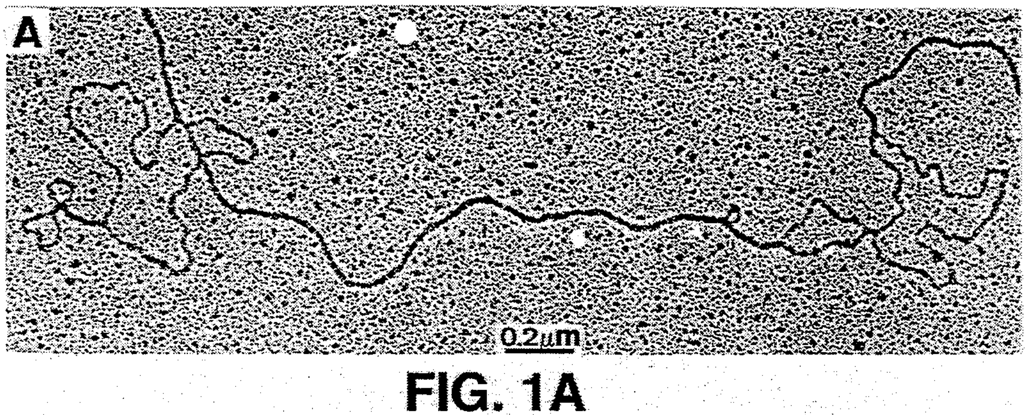
Figure 1B:
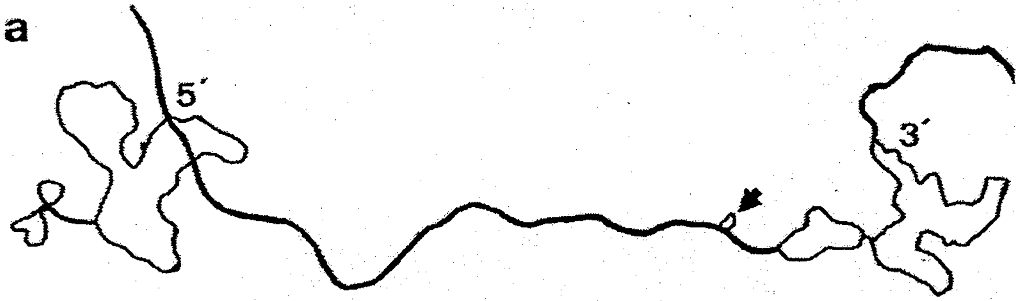

The above and various other objects and advantages of the present invention are achieved by biologically active proviral molecular clones of the BIV.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

Virus and cell culture

Bovine epithelial trachea (EBTr) cells used for the propagation and molecular cloning of BIV were obtained from the American Type Culture Collection (Rockville, Md.). For microinjection tests, primary cultures established from fetal cells of various tissues of a first trimester male bovine fetus were used. Cells were grown in Dulbecco's modified Eagle's medium supplemented with 10–15% fetal calf serum, 1% Penicillin/-streptomycin, and 1% glutamine in a humidified atmosphere of 5% $CO_2$ at 37° C. BIV is cytopathic for EBTr cells, the most notable effect being syncytium induction and cell death, and EBTr or other primary bovine cells infected with BIV do not form continuous cell lines and express virus for only a few passages; thus, it is difficult to study the long-term effects of BIV infection in vitro. To subculture and amplify the infection, and in order to obtain sufficient quantities of Infected cell DNA for cloning experiments, BIV-infected and uninfected EBTr cells were cultured at a ratio of 1:10 when maximum cytopathic effect was observed in infected cultures.

Propagation of BIV-infected cells for the large scale production of virions was performed as follows. BIV-infected EBTr cultures were split into T-150 flasks (typically, 50–100 flasks/run) at a 1:10 ratio when confluent and the cultures appeared to have 25–50% of the cells involved in syncytium formation, which is just prior to the period of maximum virus production. Uninfected-EBTr cells from confluent cultures were also split 1:10 and added to flasks containing BIV-infected cells. The media and environmental conditions were as described above with the exception that the serum requirements were dropped from 10–15% to 5–10%. When 25–50% of the culture showed involvement in syncytium formation, the culture media was harvested and replaced with fresh media every two days thereafter. This routine was performed until large numbers of cells which had become incorporated into syncytia began to show signs of coming off the substrate. Typically, this allowed for 3 harvests of the infected T-150 flasks. At this time, the BIV-infected cultures were split 1:10 into new T-150 flasks and uninfected cells were added as described above. This cycle was repeated several times. Each flask contained 15–30 ml of the media. The decanted media from the infected cell cultures was stored at 4°–10° C. until processed for virus. Virus purification (1000–5000 X concentrates) from the infected cell supernates was as described by Benton et al. (*In Vitro,* 1978, 14:192–199).

Reverse transcriptase assay

Reverse transcriptase (RT) assays were performed as described by Gonda et al [1987, *Nature* (London) 330, 388–391] using protocols of Hoffman et al (1985, *Virology* 147, 326–335).

RNA and DNA isolation

For the preparation of viral RNA, 1 ml of 1000x concentrated sucrose-gradient banded virus was brought to 1% final concentration in sodium dodecyl sulfate. Proteinase K was added to a final concentration of 0.5 mg/ml and incubated for 30 min at 50° C. The solution was then extracted three times with equal volumes of buffer-saturated phenol, followed by two extractions with a mixture of chloroform and isoamyl alcohol (24:1). The aqueous phase was adjusted to 0.3M sodium acetate and RNA was precipitated at −20° C. with 2 vol of cold ethanol. The viral RNA pellet was resuspended in 1 ml of 10 mM Trts buffer (pH 8.0), 0.1 mM EDTA (TLE). The extraction and precipitation steps were repeated and the final RNA pellet was resuspended in 100 μl of TLE. All aqueous solutions were made with glass distilled, deionized water treated with diethylpyrocarbonate and autoclaved before use to inhibit RNase activity.

Total genomic DNA was isolated from BIV-infected EBTr cells 96 hr after subculturing the infection. Six T-150 flasks containing confluent monolayers of BIV-infected cells were decanted of medium and washed gently once in 1X Dulbecco's phosphate-buffered saline. The wash was drained from the flask completely by inversion and 3 ml of lysing buffer (0.6% sodium dodecyl sulfate, 20 mM Tris buffer, pH 8.0, and 50 mM EDTA) was added. The flask was gently agitated to evenly distribute the liquid and to lyse the cells for 30 min at room temperature (22°–24° C.). The flask was placed on end for 5 min to concentrate the cell/DNA slurry and the liquid containing DNA was collected and twice extracted with equal volumes of buffer-saturated phenol/chloroform (1:1) followed by chloroform/isoamyl alcohol (24:1). DNA was ethanol precipitated by the addition of 2 vol of −20° absolute ethanol to the recovered supernatant, spooled on a Pasteur piper, and washed extensively with cold 70% ethanol. Spooled DNA was allowed to partially dry under negative pressure and then was dissolved in 10 mM Tris (pH.8.0), 1 mM EDTA at 4°–10° C. overnight. DNA from other uninfected and BIV-infected bovine cells was extracted similarly.

Library preparation and screening

A representative genomic library in the bacteriophage vector EMBL3 (Frschauf et al, 1983, *J. Mol. Biol.* 170, 827–842) was prepared from BIV-infected EBTr-cell DNA after partial digestion with Mbol and size selection (14- to 24-kb fragments) on sucrose density gradients (Maniatis et al, 1982, "Molecular Cloning: A Laboratory Manual," pp. 270–294. Cold Spring Harbor Laboratory, Cold Spring Harbor). This size range would have excluded packaging of unintegrated viral DNA. The library was packaged into infectious particles using Gigapack Gold packaging extracts according to the directions of the supplier (Stratagene). When titered on *Escherichia coli* strain KH802, the packaging efficiency of the library was $1.7\times10^6$ plaque-forming units (PFU) per microgram of ligated DNA. Library aliquots were plated at high density (60,000 PFU/150-mm dish) and screened by hybridization with radioactive cDNA probes made to viral RNA as described below (Benton and Davis, 1977, *Science* 196, 180–182; Maniatis et al, supra). Positive clones were plaque purified through two more rounds of hybridization and screening at successively lower plaque densities (10,000 and 500 PFU/150-mm dish). Replicate nitrocellulose filters were lifted and probed for each screen.

Radioactive probes

A representative cDNA probe was made from viral RNA using AMV reverse transcriptase (Bethesda Research Laboratories) as described by Mullins et al (1980, *Nucleic Acids Res.* 8, 3287–3305). Three hundred micrograms of uninfected cellular RNA per microgram of reverse-transcribed viral RNA was added as an unlabeled competitor to hybridizations in which cDNA probes were used. Probes specific for the pol genes of HIV, visna virus, and BIV were radiolabeled by nick-translation (Rigby et al, 1977, *J. Mol. Biol.* 113, 237–251) of agarose gel-isolated DNA fragments derived from the pol genes of these viruses. These were 4.0-kb Sstl-EcoRI and 1.3-kb Pstl restriction fragments for HIV [Hahn et al, 1984, *Nature* (London) 312, 166–169; Ratner et al, 1985, *Nature* (London) 313, 277–284] and visna virus (Molineaux et al, 1983, *Gene* 23, 137–148; Braun et al, 1987, *J. Virol.* 61, 4046–4054) respectively. Isolation of the BIV pol-specific fragment was achieved as described herein infra.

Heteroduplex mapping and electron microscopy.

For the preparation of heteroduplexes, a mixture of linear DNA (0.1 μg each) in a 10 mM Tris-HCl, 1 mM EDTA (pH 7.2) solution was denatured in 0.1N NaOH for 10 min at 37° C. The alkali-denatured DNA was neutralized by the addition of 0.2 vol of 1M Tris-HCl (pH 7.0). Deionized formamide was added to a final concentration of 50% and renaturation at room temperature was permitted for 15–30 min. Heteroduplexes were mounted for electron microscopy by the basic protein film technique using cytochrome c (30–50 μg/ml) as the carrier protein in a hyperphase containing 100 mM TES (N-Tris-hydroxymethyl-2-amino ethanesulfonic acid), pH 8.5, 10 mM EDTA, and, to vary the stringency, 50–80% formamide. Hetero-duplexes were examined and photographed in a Hitachi H-7000 electron microscope operated at 50 kV. Thin-section electron microscopy was performed as described by Gonda et al (1985, *Science* 227, 173–177).

Subcloning of BIV proviruses

Figure 3A:
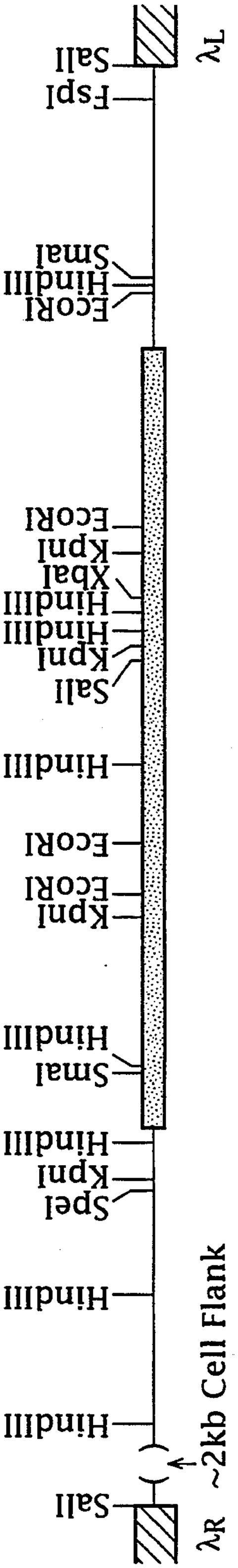
FIGS. 3A and 3B show restriction enzyme site map of BIV clone 106 and 127 respectively. SalI, SmaI, ClaI, HindIII, EcoRI, KpnI, XbaI, SpeI, and FspI were used to map clone 106; clone 127 was mapped using all but SpeI and FspI. ClaI is a noncutter in both clones and therefore is not represented on the map. The entire insert in clone 106 was mapped in relation to the SalI sites in the polylinkers at either end of the insert. Clone 127 was mapped to the first SmaI site in the right and left flanking sequences. The hatched areas and thin and bold lines are the arms, flanking DNA, and deduced BIV-specific proviral DNA sequences, respectively. The asterisk denotes the unique EcoRI site in clone 127 not represented in clone 106. The proviral genomes of clones 106 and 127 are each approximately 9.0 kb in length. Both clones are in the reverse orientation relative to the transcriptional orientation of the cloning vector. This orientation was determined from the heteroduplexes between clones of BIV and visna virus or HIV whose orientations are known. The plasmid subclones of BIV 106 and 127 were derived from segments obtained from clones 106 or 127 starting at the single SmaI site in the 5' proviral sequences and extending to the SmaI site in the 3' flanking sequences.
Figure 3B:
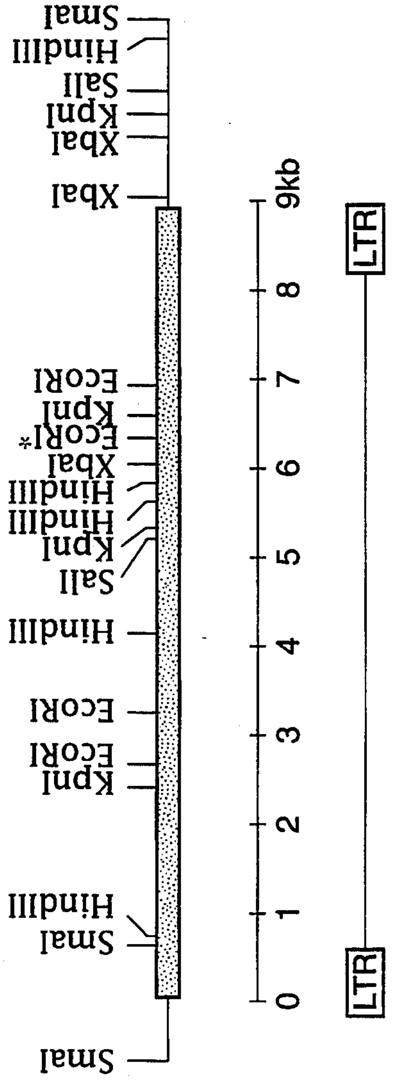

BIV clones 106 and 127 were digested with SmaI, subjected to electrophoresis in agarose, transferred to nitrocellulose according to the method of Southern (1975, *J. Mol. Biol.* 98, 503–517), and hybridized with a $^{32}P$-radiolabeled cDNA made to BIV RNA. Major hybridizing bands of 9.6 and 10.5 kb (BIV clones 106 and 127, respectively) were detected. Similar sized bands detected by ethidium bromide staining parallel experiment were excised, electroeluted, and subcloned into the SmaI site of the plasmid Bluescript (Stratagene) for further propagation and characterization. These clones contain most of the viral genome and, in addition, some cellular flanking sequences outside the 3'-most viral sequences (FIGS. 3A and 3B).

Restriction enzyme analysis of proviral DNA and plasmid BIV cloned DNAs were singly or doubly digested with various restriction enzymes under conditions suggested by the manufacturers (Bethesda Research Laboratories or New England Biolabs) and analyzed as previously described (Gonda et al, 1982, *J. Virol.* 44, 520–529). In some tests, digested DNAs were subjected to electrophoresis and transferred to nitrocellulose as described above. Virus-specific bands on filters were detected by hybridizing $^{32}P$-radiolabeled cDNA prepared to BIV-specific RNA or a nick-translated probe (Rigby et al, supra) made from the subcloned 9.6-kb SmaI fragment of BIV 106.

Microinjection

A modified version of the microinjection technique of Diacumakos [1973, "Methods in Cell Biology (D. M. Prescott, Ed), Vol. 7, pp. 287–311, Academic Press, New York] was used, as described by Boyd (1985, *Gene Anal. Tech* 2, 1–9). For individual tests, 100–200 cells were microinjected in the nucleus with DNA at a concentration of 30–50 ng/μl, and each test was repeated a minimum of four times. Several permanent mammalian cell lines stably expressing BIV have been established by this procedure and include the Cf2Th dog cell line (ATCC Cat. No. CRL1430), EREp rabbit cell line (ATCC Cat. No. CRL 6498, and BLAC-20 bovine leukocyte adherent cell line. Other methods of gene transfer including lipofection, electropotation, and transfection have also been successfully used to introduce the biologically active proviral clones of BIV Into cell lines that form a stable source of BIV. The stably infected cultures can be propagated and used for large scale virus production by standard procedures.

Sequence Analysis

For sequence analysis, the clones of BIV 106 and 127 were subcloned into plasmids. Briefly, BIV 106 was digested with the restriction enzymes FspI and SpeI. These enzymes do not cut in the proviral sequences, but do cut in the bovine host flanking sequences of the insert, adjacent to the viral long terminal repeats (LTRs), to generate a fragment of 11 kilobases (kb). This insert was isolated from gels, the ends were made flush with the Klenow fragment, and ClaI linkers were added using T4 DNA ligase. ClaI linkers were chosen for addition to the 5' and 3' termini because ClaI does not cut within the FspI-SpeI fragment (Braun et al, 1988, *Virology* 167:515–523). The resulting modified DNA, containing the complete BIV 106 proviral DNA sequences, was cloned into the ClaI site of pBluescript (Stratagene) for further propagation and analyses. BIV 127 was digested with ClaI and a 17 kb fragment containing the BIV 127 proviral sequences was isolated from gels and cloned into the ClaI site of pBluescript (Stratagene) using a procedure similar to the one described above for BIV 106. The resulting plasmids contain functional BIV 106 and 127 proviruses and are designated herein $pBIV106^{inf}$ and $pBIV127^{inf}$, respectively. The biologic activity of the proviral inserts contained in these plasmids was determined by digesting the DNA with ClaI and microinjecting the digested material into permissive cells, as previously described for BIV clones (Braun et al, supra). Cells thus manipulated formed syncytia within 24–48 hr, and supernates from these cultures were positive for RT activity within two weeks. This biologic activity could be passed to other permissive bovine cell cultures by cell-free supernates, thus verifying the functionality of the $pBIV106^{inf}$ and $pBIV127^{inf}$ clones used for sequencing.

Nucleotide Sequencing

The proviral genomes of $pBIV106^{inf}$ and $pBIV127^{inf}$ were sequenced by the dideoxynucleotide chain termination method (Sanger et al, 1977, *Proc. Natl. Acad. Sci. USA* 74:5463–5468) from random-shotgun libraries (Deininger, P. L., 1983, *Anal. Biochem* 129:216–223) in the M13 vectors mp18 or mp19 (Norrander et al, 1983, *Gene* 26:101–106) using an M13 universal primer and Sequenase version 1.0 or 2.0 (United States Biochemicals) according to the manufacturer's recommendations. The entire 11 kb ClaI fragment was used to generate a random-shotgun library for sequencing $pBIV106^{inf}$. The 17 kb ClaI fragment of $pBIV127^{inf}$ was further digested by SmaI or SmaI and XbaI to generate smaller fragments free of excess flanking sequences (Braun et al, supra). The resulting fragments were a SmaI segment (1.2 kb) containing 5' host flanking sequences and LTR; a SmaI to XbaI segment (5 kb) containing primarily gag, pol, "central region", and 5'-env sequences, and a XbaI to XbaI segment (3 kb) containing the remaining env, 3' LTR, and host flanking sequences. Independent random-shotgun libraries for sequencing were made of the 5 and 3 kb segments and a previously described 9.5 kb SmaI clone (Braun et al, supra) encompassing nucleotides (nt) from both the 5 and 3 kb fragments of $pBIV127^{inf}$. The entire 1.2, 3, and 5 kb segments were also cloned into the SmaI and/or XbaI site(s) of M13 mp18 or mp19 for site-directed sequencing and walking with oligonucleotide primers for sequence confirmation or to fill in gaps where necessary. Ambiguities and compressions were resolved by the use of Taq polymerase (Promega Corporation), with or without deaza-GTP, and Sequenase with dITP according to the manufacturers' recommendations. The entire proviral sequences for BIV 106 and 127 were determined on both strands and each base was sequenced an average of 8 times. The possibility of clustered SmaI or XbaI sites at the Junctions of the 1.2 and 5 or the 5 and 3 kb segments, respectively, of BIV 127 was ruled out by comparison to BIV 106 sequence generated from the random-shotgun library and by sequencing in M13 additional BIV 127 subclones, generated by digestion with restriction enzymes other than SmaI or XbaI.

Computer Analyses

The nucleotide sequences of the proviral genomes were reconstructed using the computer programs of Staden (1982, *Nucl. Acids Res.* 10:4731–4751). Nucleotide sequences and translations of BIV 106 and 127 were analyzed using the UWGCG suite of genetic analysis programs (Devereaux et al, 1984, *Nucl. Acids Res.* 12:387–395) run on a DEC VAX 8600 (Advanced Scientific Computing Laboratory, NCI-FCRF). The published nucleotide sequences of the other lentiviruses [HIV-1 (Ratner et al, 1987, *AIDS Research and Human Retroviruses* 3:57–69), HIV-2 (Guyader et al, 1987, *Nature* 326:662–669), $SIV_{mac}$ (Chakrabarti et al, 1987, *Nature* 328:543–547), $SIV_{agm}$ (Fukasawa et al, 1988, *Nature* 333:457–461), visna virus (Braun et al, 1987, *J. Virol.* 61:4046–4054), and EIAV (Kawakami et al, 1987, *Virology* 158:300–312)] used in analyses were obtained from GenBank. The peptide sequences were inferred from the nucleotide sequences using UWGCG Translate.

Primer Extension

To determine the cap site of the viral RNA, a simulated strong stop cDNA was synthesized using an oligonucleotide (20-met) primer with the sequence 5′-TGTTGGGTGTTCTTCACCGC-3′, representing the complement of nt 186–205 of the BIV 127 provirus (186 nt from the predicted transcription initiation site), and total cellular RNA from BIV-infected cultures. Briefly, the oligonucleotide primer was labeled at the 5′ end using T4 polynucleotide kinase and [$\gamma^{32}P$]ATP (Maniatis et al, 1982, Molecular cloning: A laboratory manual, p. 125–126. Cold Spring Harbor Laboratory Press, Cold Spring Harbor, N.Y.). Following phenol-extraction and ethanol precipitation, 0.2 pmol of primer was combined with 5 μg total RNA from uninfected BLAC20 cells or BLAC 20 cells infected with BIV 106, BIV 127, or parental stocks in annealing buffer consisting of 80% formamide, 0.4M NaCl, 0.04M PIPES pH 6.4, and 0.001M EDTA (Casey et al, 1977, *Nucl. Acids Res.* 4:1539–1552). The primer and RNA were annealed by heating to 70° C. for 10 min. followed by slow cooling (60 min) to 37° C. The annealing reactions were diluted 10-fold into RT buffer (0.05M Tris-HCl, pH 8.5, 10 mM $MgCl_2$, 0.04M KCl, 1 mM DTT, and 0.5 mM dNTP), Mo-MuLV RT (200 U) (Bethesda Research Labs) was added and the reactions incubated at 37° C. for 60 min (Calzone et al, 1987, *Meth. Enzmol.* 152:611–632). The reactions were phenol extracted, ethanol precipitated, and analyzed on a 6% polyacrylamide sequencing gel containing 7M urea. A sizing ladder of BIV 106 sequence was created by sequencing an M13 template that spanned the $U_3$—R Junction, R and $U_5$ elements, and the $U_5$-untranslated region, using the same labeled 20-mer as in the primer extension reactions and electrophoresing it in lanes adjacent to the primer extension reactions (Sanger et al, 1977, *Proc. Natl. Acad. Sci. USA* 74:5463–5468).

RESULTS

Initial library screening

A library aliquot of $2.8\times10^6$ recombinant phage was screened for hybridization to a cDNA probe made from BIV viral RNA. Eighteen eDNA-hybridizing plaques were isolated as potential BIV proviral clones. Only two clones, 56 and 39, hybridized with these heterologous probes. Heteroduplex mapping of these clones to each other showed approximately 6.0 kb of homologous DNA that remained annealed at high stringency (FIG. 1A). It was presumed that this homologous segment represented a portion of a BIV provirus. The proviral element was truncated at one end in one clone but in the other clone was flanked on both sides by nonhybridizing segments presumed to be derived from bovine cellular sequences. Additionally, the proviral element in one clone was interrupted by a 500-bp deletion/substitution loop (FIG. 1A).

Figure 1C:
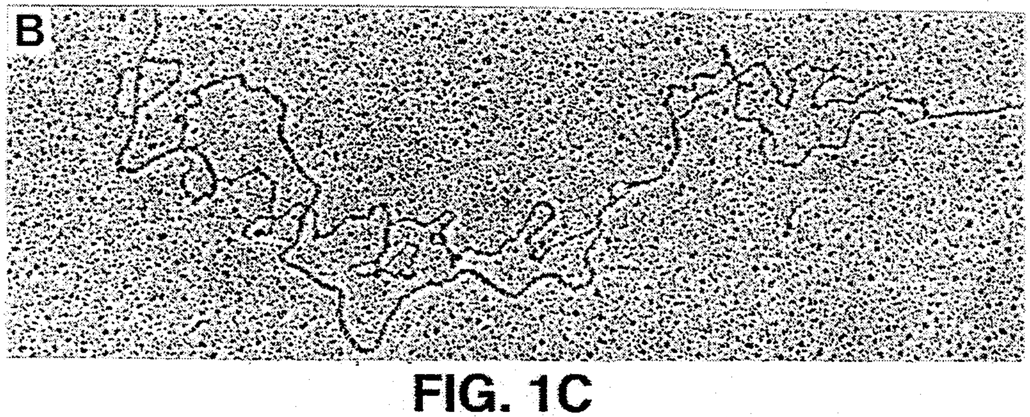
FIGS. 1C and 1D show heteroduplex analyses (B) between BIV clones 56 and visna virus. Heteroduplexes were prepared with inserts in the vector EMBL 3 (clones 39 and 56) or WES. (visna clones.)
Figure 1D:
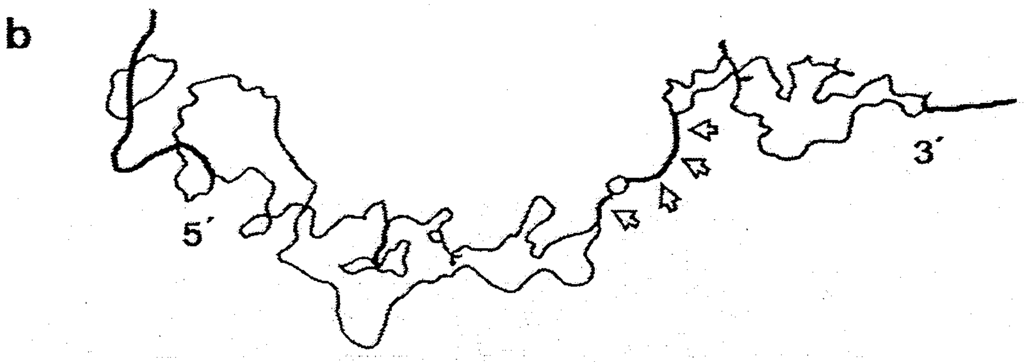

Low stringency heteroduplex mapping with cloned genomes of visna virus (FIG. 1C) and HIV (data not shown) demonstrated that clones 39 and 56 shared about 1 kb of cross-hybridizing sequences with these two viruses in a similar pattern. This hybridization mapped to the amino terminus of the pol region of both HIV and visna virus. Moreover, these heteroduplexes demonstrated that clone 39 was truncated and that clone 56 had the potential to be a full-length provirus. Attempts to demonstrate biological function of the proviral sequences in clone 56 by microinjection or transfection of the cloned DNA into BIV-susceptible cells were unsuccessful. In later heteroduplexes formed with biologically active clones described below, it was found that the 500-bp deletion seen in heteroduplexes between clones 56 and 39 definitely resided in clone 56 (data not shown).

Derivation of a BIV pol probe

At this point, it was clear that a pol-specific probe may be useful in attempts to isolate an infectious BIV proviral clone because it would hybridize only to those clones containing the central portion of the provirus. Such clones would be a subset of all provirus-containing clones and would be more likely to be full length than clones selected by a probe representing the entire BIV genome.

Accordingly, a BIV pol-specific probe was isolated by first constructing a random shotgun library of sonication fragments from BIV clone 56 in the M 13 vector mp 18 (Deininger, 1983, *Anal. Biochem.* 129, 216–223; Norrander et al, 1983, *Gene* 26:101–106). Then this M 13 library was screened for clones hybridizing at low stringency to pol probes from HIV and visna virus. Twenty clones were identified, isolated, and sequenced. Most of these clones overlapped, establishing the sequence of the highly conserved core reverse transcriptase domain at the amino terminus of the BIV-pol gene [Gonda et al, 1987, *Nature* (London) 330:388–391]. This sequence conclusively demonstrated that BIV clone 56 contains a retroviral provirus, that this provirus was not derived from any previously sequenced retrovirus, and that BIV belongs to the lentivirus subfamily. Then a 420-bp KpnI-BamHI fragment from one of the M13 sequencing clones was subcloned into the plasmid vector Bluescribe M13+ (Stratagene) for use as a BIV pol-specific probe. This fragment extends from an upstream KpnI site across the core reverse transcriptase domain and terminates at a BamHI site in the M13 polylinker.

Isolation of biologically active proviral clones

The 420-bp BIV pol-specific probe was used to screen an additional $1\times10^7$ recombinant phage from the same library of BIV-infected EBTr cell DNA. Twenty-one plaques positive for pol hybridization were isolated.

Figure 2A:
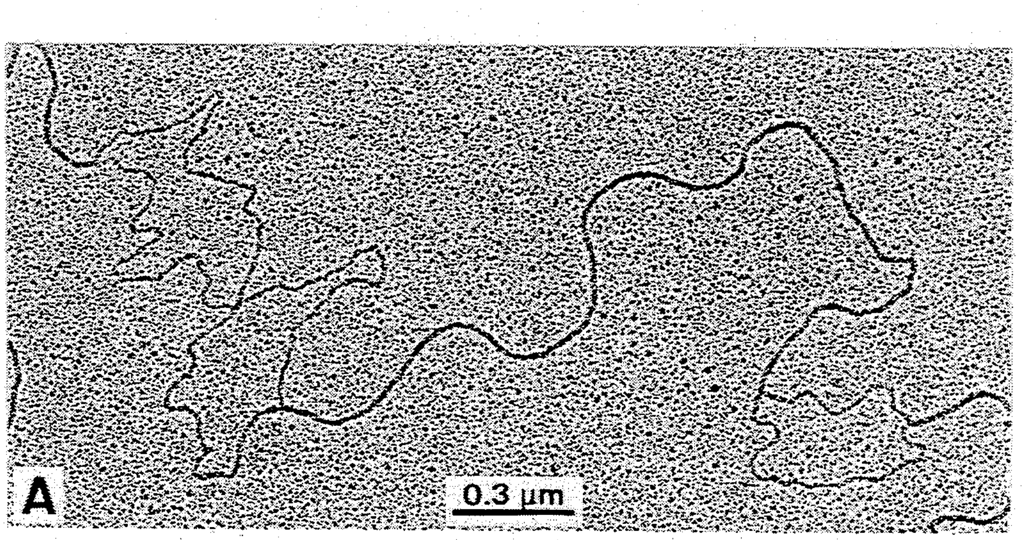
FIGS. 2A and 2B show heteroduplex analysis of biologically active BIV clones 106 and 127. Heteroduplexes were prepared with inserts in the vector EMBL 3.
Figure 2B:
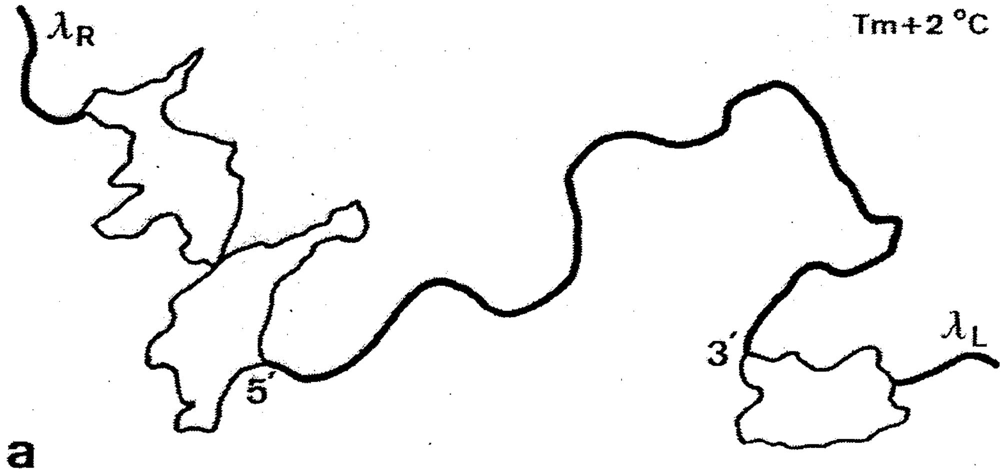

The position and size of proviral elements in these clones were mapped by heteroduplex formation with BIV clone 56 and with each other. The heteroduplexes revealed defects in most clones, such as deletions, truncations during provirus insertion, and truncations during cloning that would prevent biological function. However, two clones, 106 and 127, had proviral elements that formed heteroduplexes greater than 8.0 kb in length with BIV clone 56 and approximately 9.0 kb in length with each other (FIGS. 2A and 2B). The proviruses in these clones were flanked on both ends by unrelated cellular sequences and therefore appeared to be good, candidates for full-length infectious units.

Restriction enzyme site maps were inferred from single- and double-enzyme digests of DNA from BIV clones 106 and 127 (FIGS. 3A and 3B respectively). In agreement with the heteroduplexing results, the two clones are approximately 9.0 kb in length and share 13 of 14 sites mapped within the provirus (a unique EcoRI site resides in the 3′ half of the BIV 127 genome), but differ at all sites mapped in the cellular flanking sequences. Although all sites conserved in the provirus restriction enzyme maps appear to be the same in both clones, electrophoresis experiments, demonstrated that a 1.2-kb 3′ KpnI segment (KpnI segment from 5.3 to 6.5 kb in the BIV 127 provirus map shown in FIG. 3B) was consistently 100 bp larger in the BIV 127 plasmid subclone than the corresponding segment in the BIV 106 plasmid subclone. Moreover, the size of the KpnI-EcoRI segment (map positions 6.5 and 6.8 kb, respectively, in BIV 106 and 127) remained the same size (300 bp) in both clones. The unexpected size difference suggests that the BIV 127 provirus contains approximately 100 bp more information than BIV 106. Since no other migration anomalies were noted between the two clones in other areas of the provirus, it was deduced that the additional sequences in BIV 127 reside between the HindIII and KpnI sites (BIV 127 provirus map positions 5.8 and 6.5 kb, respectively; FIG. 3B) and probably in close proximity to the unique EcoRI site located in the 3′ half of the genome.

The unique EcoRI site in clone 127 allowed us to go back to the original virus stock and diagnostically determine which of the two clones, if either, was the predominant provirus species relative to EcoRI. Total genomic DNA of cells independently infected with BIV parental stock, clone 106, or clone 127 was digested with EcoRI. In Southern transfers of these DNAs, using the entire 9.6 kb SmaI fragment of BIV 106 as the probe, it was found that the parental stock and clone 106 had an Identical EcoRI virus-specific band pattern, which was distinct from that of clone 127, suggesting that BIV clone 106 is the predominant species in the parental stock (data not shown).

Biological activity of BIV clones 106 and 127

Figure 4A:
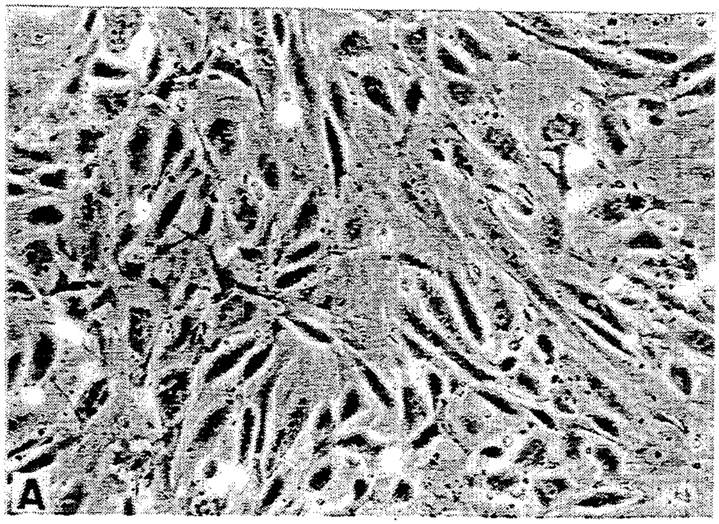
FIG. 4A shows Mock-injected BESp control cells. The photographs were taken 48 hr after microinjection of the DNA into the nucleus.
Figure 4B:
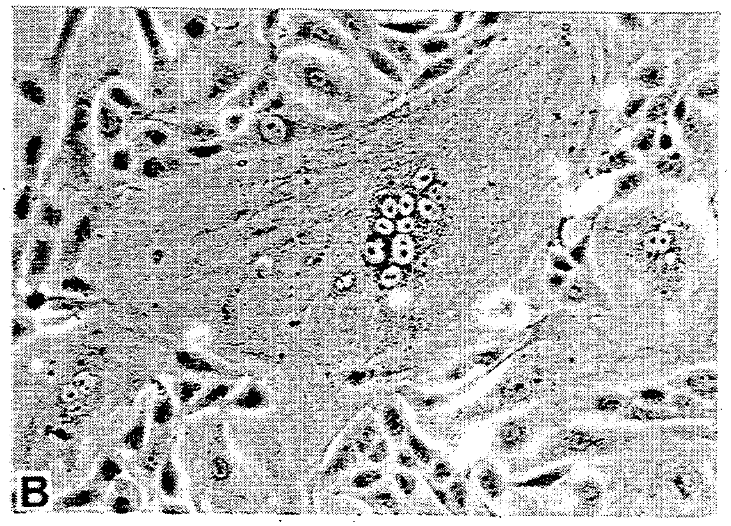
Figure 4C:
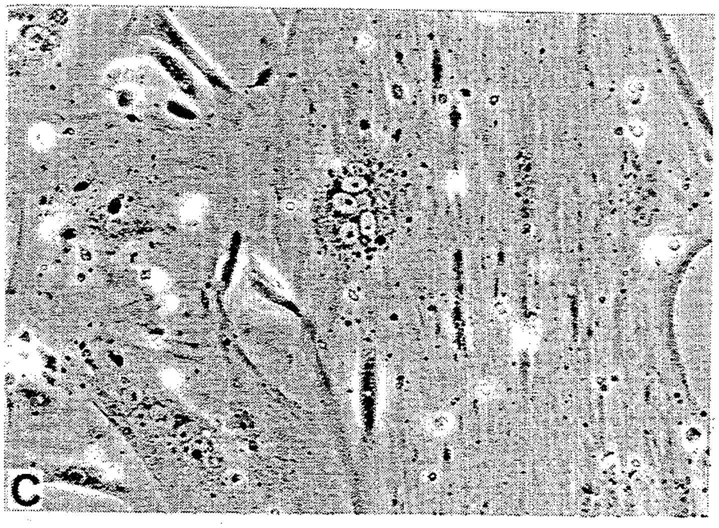

Uncut purified DNA containing clone 106 or 127 proviral sequences was microinjected into bovine embryonic spleen (BESp) cells that had been seeded at moderate density onto glass coverslips. One hundred to two hundred cells were injected on each coverslip. At 24–48 hr after injection, as the cell sheet grew to confluence, syncytium formation could be detected between adjacent cells. These syncytia typically had 5–20 nuclei, surrounded by large, flattened cytoplasmic sheets (FIGS. 4B and 4C). No syncytia were seen in uninjected control cells (FIG. 4A) or in cells injected with clone 56 or any of seven other defective clones (data not shown). Cf2Th and EREp cells were transfected with BIV 106 or 127 clones by this and various other methods of introducing DNA into cells. Not only did the Cf2Th and EREp established cell lines show the typical cytopathic effects of the virus, but they also became persistently infected and are a continuous source of BIV and BIV antigen.

After syncytia formation had reached its peak (Day 4), the coverslips in dishes were overlaid with uninfected cells or were placed in T-25 flasks containing subconfluent cultures of BESp cells to amplify the infection. Supernatant fluids from these cultures were positive for reverse transcriptase activity when assayed 10 days after microinjection, while uninjected cells, or cells injected with defective proviruses, remained negative. The ability to form syncytia and supernatant reverse transcriptase activity could be passed to other primary bovine cell cultures, but not to human cells, by cell-free supernatants from micro-injected cultures. Although subjectively obtained, the only biologically significant difference between the two clones was the aggressiveness with which the cell-free infection spread. BIV 106, in comparison to clone 127, tended to have more extensive and rapid syncytia formation in BESp cells, although virus recovered from cultures infected in parallel with titered stocks showed no quantitative differences in reverse transcriptase activity. Nevertheless, both BIV 106 and 127 are more aggressive in vitro than parental stock from which they were cloned (data not shown).

Figure 5A:
FIGS. 5A–5C shows electron micrographs of BIV produced in BESp cells microinjected with clone 106 DNA.
Figure 5B:
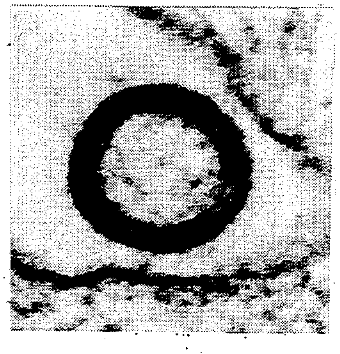
Figure 5C:
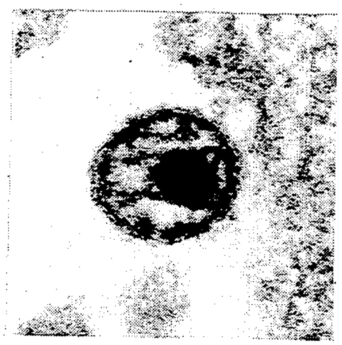

Budding and mature virus particles could be visualized by electron microscopy in cell cultures microinjected with either clone 106 (FIGS. 5A–5C) or 127. These particles closely resembled those present in uncloned BIV stock cultures.

Nucleotide Sequence of BIV 106 and 127

The complete nucleotide sequences and translations of BIV 106 and 127 are shown in FIG. 6. The genome of BIV 127 is 8,482 nt in the form of the viral RNA; BIV 106 is slightly smaller at 8,391 nt. This difference is explained by the fact that BIV 106 has suffered a major (87 nt; nt positions 5819–5905) and two minor (4 nt; nt positions 99–100 and 8470–8471) deletions relative to the BIV 127 genome. Numerous substitutions are also prevalent as listed in Table 1. Because BIV 127 contains a significantly greater amount of genetic information, It is considered to be the prototypic sequence from which BIV 106 was derived.

Genetic Organization

The genetic organization of BIV (FIGS. 7A–7C) is similar to that of other lentiviruses. There are three large and several smaller open reading frames (ORFs). The overall topography for the BIV genome is:

5′LTR-gag-pol-"central region"-env-3′LTR.

Figures 7A, 7B, 7C:
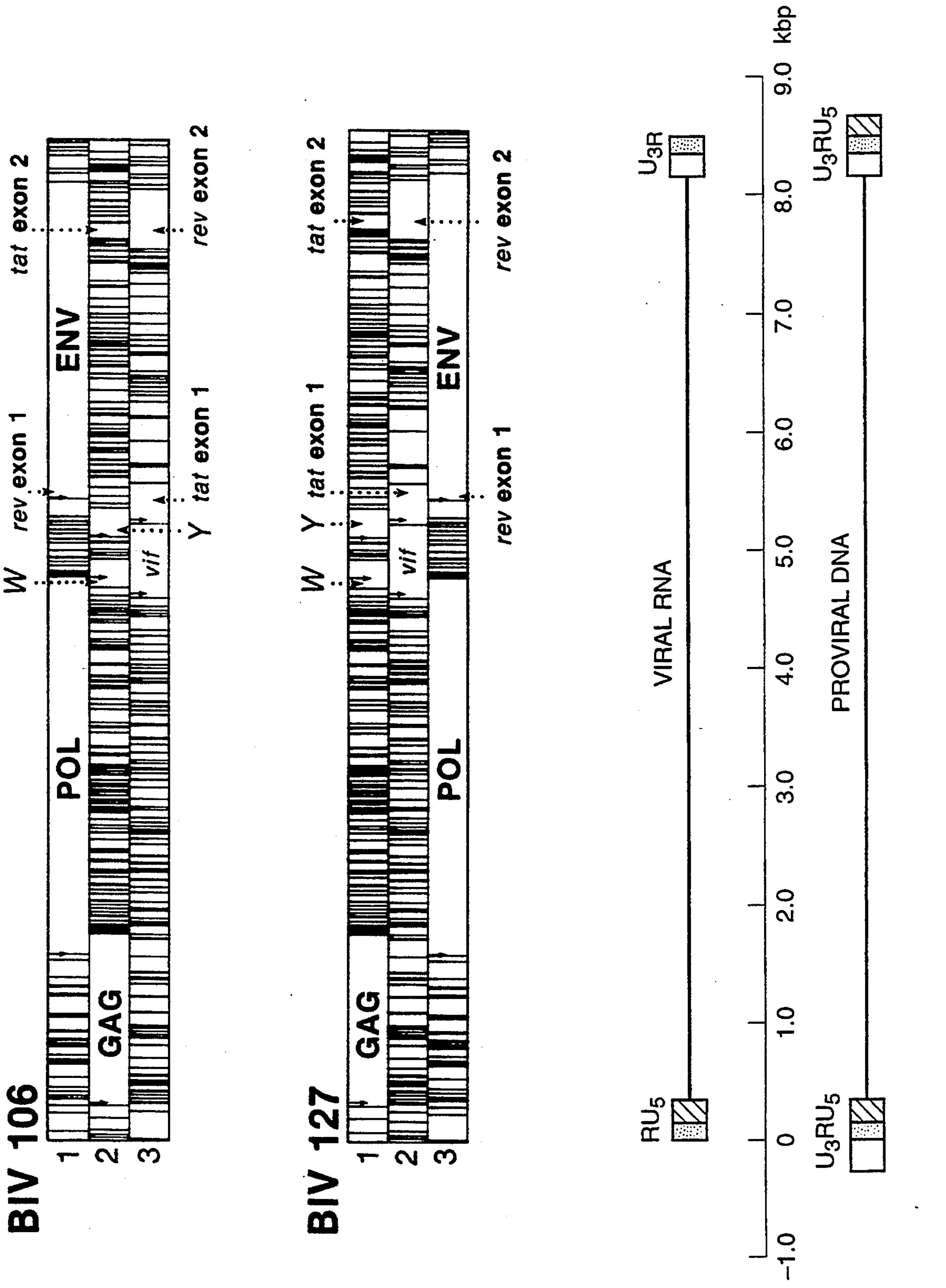
FIGS. 7A–7C show the comparison of the genomic organization of BIV 106 and 127 biologically active clones deduced from ORF analysis of the nucleotide sequence presented in FIGS. 6A–6D. Translation of the sequences in each reading frame commenced at nucleotide (nt) 1. Vertical bars represent stop codons. Arrows indicate the initiator AUG codon in viral genes or putative genes. ORFs annotated are gag, pol, env, vif, tat. exons 1 and 2, rev exons 1 and 2, W, and Y. Location of LTR boundaries in the viral RNA and proviral DNA are indicated above and below the kb marker, respectively.

The three larger ORFs encode genes with structural or enzymatic function and are in the invariant order gag, pol, and env, present in all replication-competent retroviruses. The gag and pol genes are in different reading frames and overlap. The pol and env genes are in the same reading frame and are separated by the "central region", the hallmark of lentiviruses (Braun et al, 1987, *J. Virol.* 61, 4046–4054; Chakrabarti et al, 1987, *Nature* 328, 543–547; Fukasawa et al, 1988, *Nature* 333, 457–461; Guyader et al, 1987, *Nature* 326, 662–669;Ratner et al, 1987, *AIDS Res. Hum. Retroviruses* 3, 57–69; Sonigo et al, *Cell* 42, 369–382). The 5'-most 2 nt deletion (R region of the 5' LTR) in BIV 106 has caused a reading frame shift in all ORFs relative to BIV 127. Despite the deletions and substitutions in BIV 106, it has exactly the same overall organization as BIV 127; none of the ORFs appears to be truncated and no additional ORFs were created (FIGS. 7A–7C).

Structure of the LTR

Figure 8:
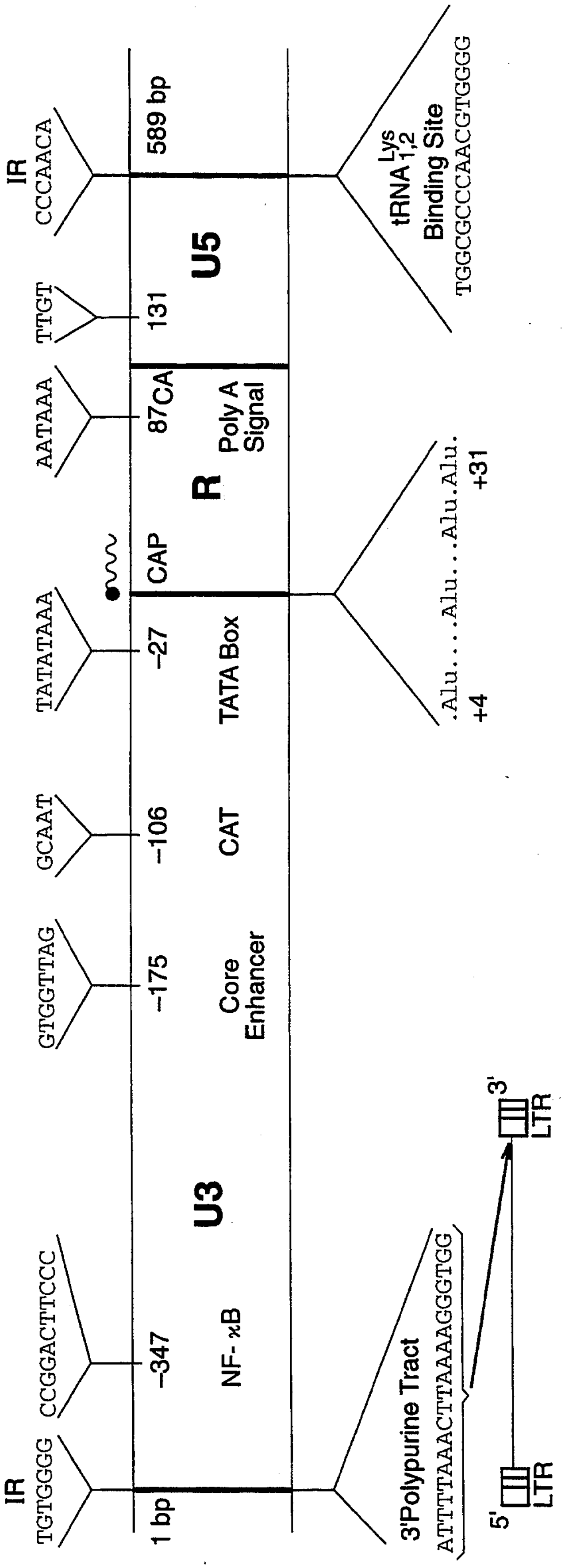
FIG. 8 shows the organization of BIV 127 LTR. Boundaries of the $U_3$, R, and $U_5$ regions are indicated as well as the nucleotide positions of the TATA and CAT boxes, core enhancer, polyadenylation signal and poly(A) addition site (CA) at the $R-U_5$ boundary, cap site at the $U_3-R$ boundary with repeated Alu recognition sites, tRNA primer binding site, polypurine tract, potential NF-kB site, and imperfect inverted repeat (IR) beginning at the dinucleotide (5'TG and 3'CA) of LTR boundaries.

The proviral LTRs of BIV 127 and 106 are 589 and 587 nt long, respectively. In addition to the 2 nt deletion in BIV 106, there are 4 substitutions that distinguish the LTRs of the two proviral clones. The boundaries of the LTR and its internal $U_3$, R, and $U_5$ elements were determined by sequence analysis and biochemical experiments to complement the structural analysis (see below). The BIV 127 LTR is diagrammatically depicted with annotations in FIG. 8. The boundary distinguishing the retroviral LTR from internal viral sequences is indicated by the presence of a short inverted repeat 5'AC-TG3' located after a polypurine tract in the 3' end of the genome and 5'CA-GT3' located before a sequence complementary to the 3' end of the binding site for a tRNA that is used to initiate minus-strand synthesis by the viral RT. The tRNA used by BIV is tRNA $_{1,2}{}^{LYS}$ and is identical to that used by visna virus (Braun et al, supra; Sonigo et al, 1985, *Cell* 42:369–382)

Figure 9:
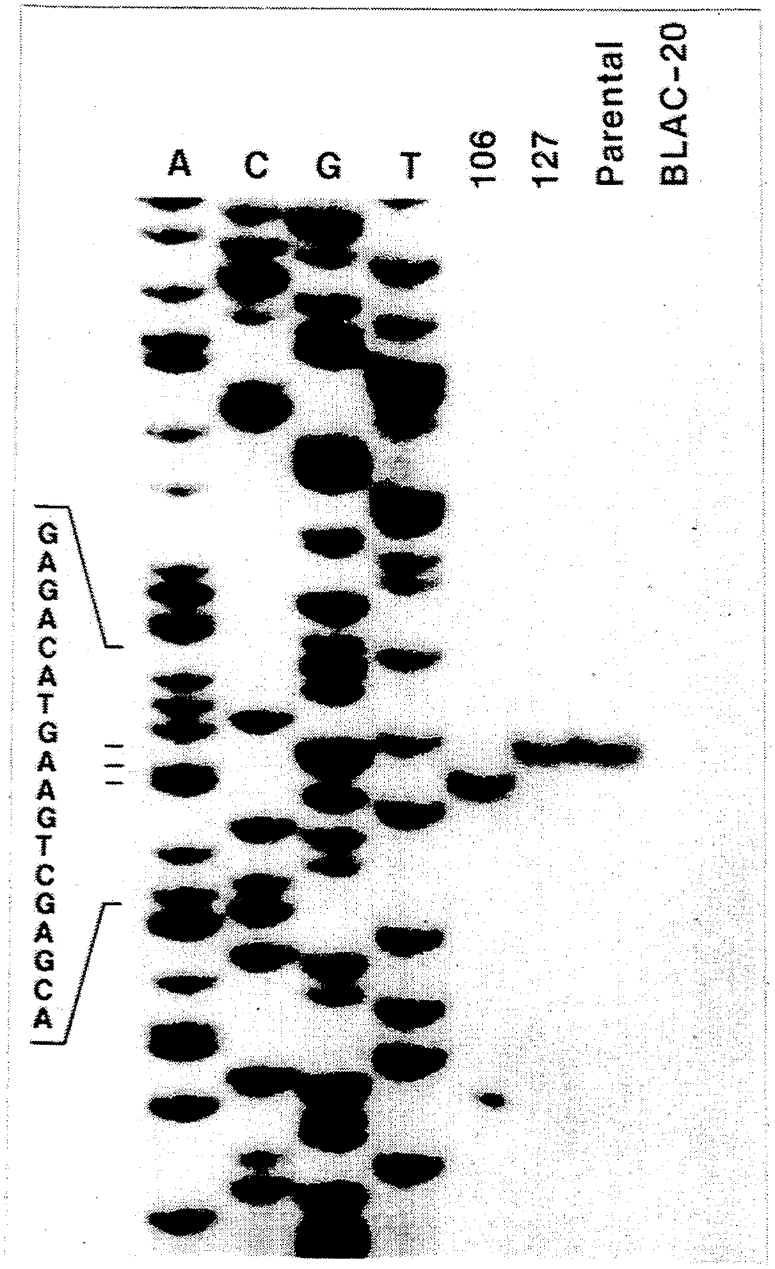
FIG. 9 shows the determination of the transcription initiation site by primer extension from viral RNAs. Lanes 1–4: Sequencing ladder (A, C, G, and T, respectively) using the nt determined for the noncoding strand of BIV 106, included for accurate estimation of the size of the extension products; lane 5: RNA from BIV 106-Infected cells; lane 6: RNA from BIV 127-infected cells; lane 7: RNA from parental BIV-infected cells; lane 8: control RNA from uninfected cells. The RNA isolation, primer extension, and sequencing reactions were performed as described in Materials and Methods.

Retroviral LTRs classically contain a long direct repeat between the $U_3$ and $U_5$ elements. For BIV 127, this element is 111 bp (109 bp for BIV 106), and structurally defines the $U_3$–R and R–$U_5$ boundaries. Strong stop cDNA was synthesized using a radiolabeled-oligonucleotide primer, RT, and viral RNA from cells independently infected by BIV 106, BIV 127, and parental virus. The primer extension reactions were compared to a dideoxy sequence ladder encompassing the BIV 106 LTR to the untranslated region 5' of the gag ORF to further deduce the size of $U_5$+R elements and the putative position of the $U_3$–R Junction corresponding to the cap site in the viral RNA (FIG. 9). The cap sites in BIV 106 and 127 were determined to be at the first T in the R element of the LTR. The length of R+$U_5$ is 203±1 nt for BIV 106 and 205±1 nt in BIV 127 and parental stocks. This value is in agreement with assignments based on structural analyses and confirms the deletion of 2 nt in the BIV 106 LTR. By computation, the deduced U+ and $U_5$ elements are therefore 384 and 94 nt, respectively, for both BIV 127 and 106.

In the $U_3$ region (FIG. 8), putative transcription-regulating signals were identified by analogy to previously defined lentivirus LTR signal sequences. Potential promoter sequences for the TATA and CAT boxes were identified. Also identified by sequence homology was a conserved sequence for a retroviral core enhancer and NF-kB binding site similar to the one within the enhancer of the k immunoglobin chain gene. Sequence homology to Sp1 binding sites (nt 8294–8302) related to that of the human metallothionein gene were found between the CAT and TATA boxes and an additional sequence homologous to an Sp1 binding site in the enhancer elements of SV40 was found in $U_5$ (nt 181–189) (FIGS. 6A–6D). Sp1 and NF-kB binding sites have been detected in the $U_3$ region of the LTRs of HIV-1, HIV-2, and SIVs (Gaynor et al, 1988, *Proc. Natl. Acad. Sci.* 85:9406–9410; Guyader et al, supra) and an NF-kB site in the U3 region of the feline immunodeficiency virus (FIV) (Olmsted et al, 1989, *Proc. Natl. Acad. Sci. USA* 86:2448–2452). Also identified were sequences (nt 8123–8131) related to the glucocorticoid receptor binding site observed in the mouse mammary tumor virus LTR (Wingender, 1988, *Nucl. Acids Res.* 16:1879–1901). The functional significance of these structurally identified transcription-modulating sequences remains to be determined.

In the R region (FIG. 8), the signal sequence for polyadenylation (AATAAA) was present 87 bp from the cap site and a poly(A) addition site (CA) was identified 18 nt from the signal sequence, marking the end of R and the R–$U_5$ boundary. Interestingly, surrounding the cap site is a series of AluI restriction enzyme recognition sequences. It is tempting to speculate that this repeated motif surrounding the cap site may be useful in providing structural conformation for regulation of transcription. gag, pol, and env ORFs The molecular weights for the precursors of the major ORFs (FIGS. 7A–7B) of BIV were calculated from the DNA sequence of BIV 127 (FIGS. 6A–6D). The processed protein products of the gag, pol, and env ORFs were deduced by homology with known HIV and other lentivirus proteins, conserved structural features such as cysteine amino acid (aa) residues, and hydropathy plots (Table 2).

The gag precursor of BIV has a calculated molecular weight of 53 kilodaltons (kd) (Table 2), which is consistent with the p53 antigen detected on Western blots (Gonda et al, 1987, *Nature* 330:388–391) and by radioimmunoprecipitation of a similar sized protein from BIV-infected mammalian cells and insect cells infected by a recombinant baculovirus containing only the gag ORF of BIV using rabbit polyvalent antisera raised to purified BIV and natural and experimental sera from BIV-infected cattle. The p53 N-terminal sequence begins with the sequence Met-Lys-Arg-Arg and is not compatible with myristoylation since the second residue of the N-terminal sequence required for the addition of myristic acid is Gly, as found in HIV-1. The p53 is probably processed, by analogy to HIV (Lillehoj et al, 1988, *J. Virol.* 62, 3053–3058) into three smaller proteins, p17, p26, and p14. The predicted size for the major capsid or core protein is 23 kd; however, previous Western blot analyses using BIV-specific antisera and purified virions have shown it to migrate as a protein of 26 kd (Gonda et al, 1987, *Nature* 330, 388–391). Until further analysis, however, the designation p26 has been retained herein for consistency. The p17 or matrix protein would reside on the amino terminus side of p26. At the carboxy terminus of the gag precursor and within the predicted p14 reside two copies of a cysteine-rich motif (CX—$X_2$—C—$X_4$—H—$X_4$—C) (gag amino acids 405–418 and 423–436) reminiscent of the "zinc finger" seen in nucleic acid-binding proteins of other retroviruses (Berg, 1986, *Science* 232:485–486; Covey, 1986, *Nucl. Acids Res.* 14:623–633; Evans et al, 1988, *Cell* 52:1–3; Henderson et al, 1981, *J. Biol. Chem.* 256:8400–8406; Oroszlan et al, 1985, *Curr. Top. Microbiol. Immunol.* 115:221–223). Moreover, the DNA binding proteins usually reside to the carboxy terminus of the major gag protein (here p26); therefore, it is postulated that p14 is the nucleocapsid protein of BIV.

Segments of the pol gene, in particular RT and endonuclease, are the most conserved in the evolution of retroviruses, and homologies between the amino acid sequences of the predicted translated proteins of various species are readily detected (Chiu et al, 1985, *Nature* 317 366–368; Gonda et al, 1989, *Arch. AIDS Res.* 3:1–42;

Gonda, In: Applied Virology Research: Vol. 2-Virus Variation and Epidemiology. Plenum Publishing, New York, N.Y. (in press); Gonda et al, 1986, *Proc. Natl. Acad. Sci. USA* 83 4007–4011; Sonigo et al, supra). In the pol ORF are the protease, RT and endonuclease coding regions of the virus (Table 2). The pol precursor of BIV is predicted to be 121 kd. The protease (p11), RT (p72), and endonuclease (p32) proteins have been localized in the translation of the pol ORF (FIGS. 6C–6I) by homology to those of HIV and other lentiviruses. The PD1 ORF products have not yet been immunologically detected.

The immunologic cross-reactivity of the gag gene products of BIV and HIV-1 has been localized to p24 and p26 of HIV and BIV, respectively (Gonda et al, supra). In molecular hybridization experiments, positive hybridization of cloned lentiviral sequences has been found mainly with the pol gene (Gonda et al, supra; Olmsted et al, upr). Thus, it was anticipated that the predicted gag and pol proteins of BIV would have detectable amino acid homology to those of other lentiviruses. However, when BIV 127 translation products for gag and pol ORFs were globally compared to those of other lentiviruses, only a small amount of homology was found when identical amino acid residues were calculated (range for gag=23–29%; pol=36–38%). The percentage of matching residues increased significantly when conservative amino acid substitutions were included (range for gag=48–55%; pol=59–61%). Nevertheless, at least for the pol ORF, there were regions of locally strong sequence conservation, especially in the RT and the endonuclease domains of pol.

To account for the immunologic cross-reactivity between BIV and HIV-1 gag proteins, a local homology comparison of the predicted capsid segments for this ORF was made. Only one stretch of 10 amino acids within the p26 of BIV was observed to have a high degree of homology to HIV-1; this area was also compared to several other lentiviruses (FIG. 10). Within this stretch, BIV shared 8 of 10 residues with EIAV, 7 of 10 with HIV-1, HIV-2, and $SIV_{agm}$, 6 of 10 with $SIV_{mac}$, and only 3 of 10 with visna virus. It is worth noting that only $SIV_{mac}$, HIV-1, and EIAV compete in heterologous competitive radioimmunoassays using radiolabeled HIV p24 and rabbit polyclonal antisera to BIV (HIV-2 and $SIV_{agm}$, have not been tested); and, BIV and HIV-1 core proteins do not exhibit immunological cross-reactivity with visna virus in Western blots (Gonda et al, supra). The homologous region in the p26 of BIV gag (FIG. 10) may be the epitope(s) responsible for the immunologic cross-reactivity between BIV, EIAV, and the primate lentiviruses. Using computer algorithms to test this hypothesis (Jameson et al, 1988, *CABIOS* 4:181–186), this conserved segment of BIV 127 was found to have a high surface probability, a feature of peptides predicted to be potential antigenic determinants (data not shown).

Figure 11A:
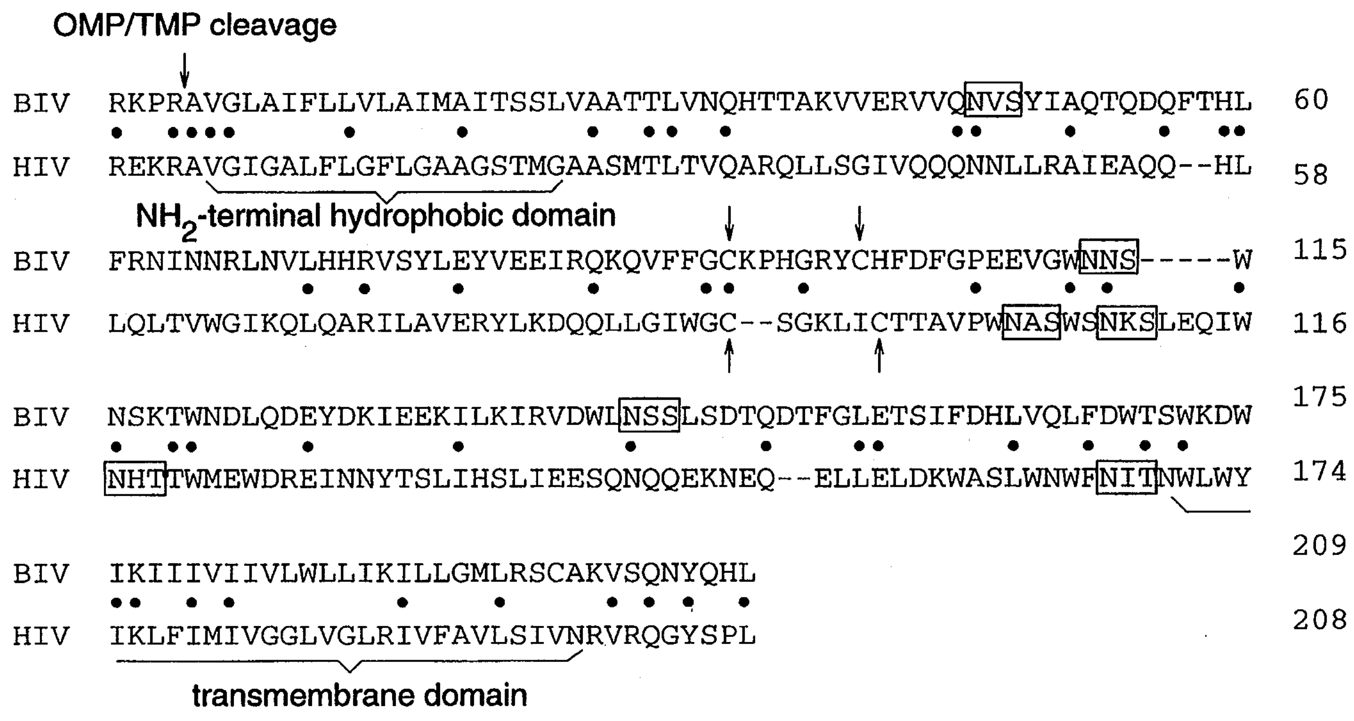
FIGS. 11A–11C show the comparison of the transmembrane proteins (TMP) of BIV 127 and HIV-$1_{HXB2}$.

The BIV env precursor is predicted to be 102 kd in its unmodified form (Table 2). The first hydrophobic stretch of amino acids which might represent the leader sequence is located 50 amino acids into the translation of the env ORF in the vicinity of the second Met as deduced from hydropathy plots. It has not been determined whether the second or the first Met in this ORF represents the beginning of the translation of the env protein (see discussion below on rev). The addition of sugar residues by N-linked glycosylation substantially increases the molecular weight of the envelope protein backbone in lentiviruses and may account for up to 50% of the apparent molecular weight, making them the largest retrovirus env products characterized (Pyper et al, 1984, *J. Virol.* 51:713–721; Robey et al, 1985, *Science* 228:593–595). The BIV 127 env precursor has 21 potential glycosylation sites. It is predicted to be cleaved into an outer membrane protein (OMP) and transmembrane protein (TMP) after the Arg-Lys-Pro-Arg site (aa 552–555; FIGS. 6m and 11a). This putative cleavage site and the area around it are partially conserved (5 of 7 aa) with that of HIV-1 (FIG. 11a). The cleavage products of BIV 127 env are predicted to be 62 kd and 40 kd for the OMP and TMP, respectively. Proteins in the range of 100 kd and 45 kd have been detected in Western blots and a 100 kd protein has been immunoprecipitated using serum from naturally- or experimentally-infected cattle. The larger is believed to be the glycosylated OMP and the smaller the TMP of the virus by analogy to other lentiviruses. The precursor from which they are derived has not been observed.

Figure 11B:
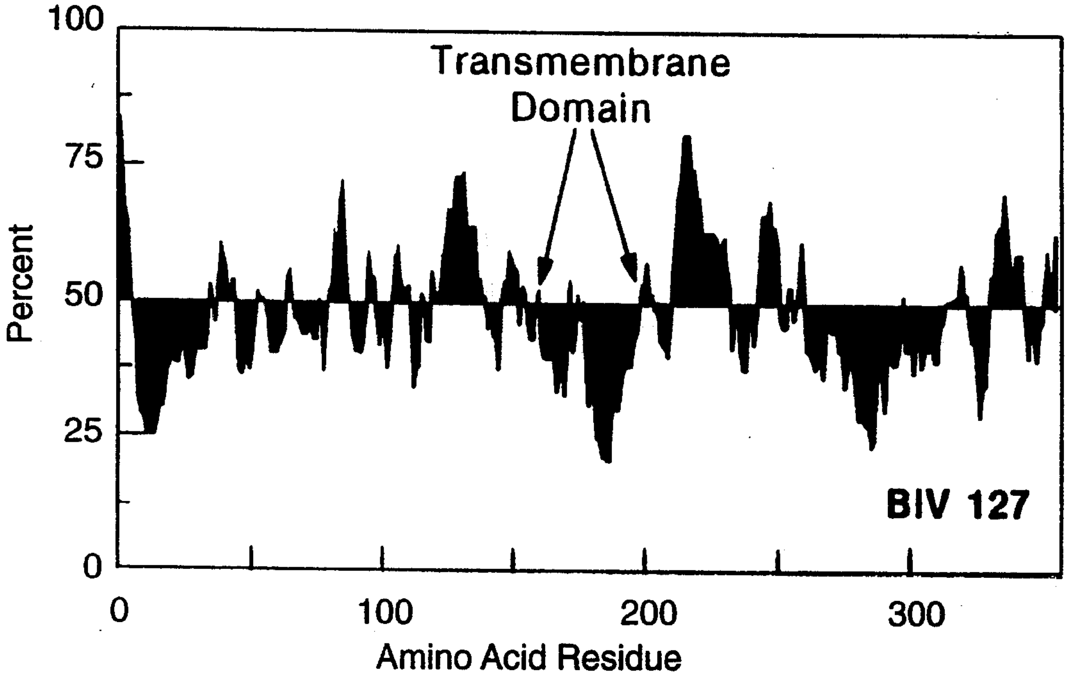
Figure 11C:
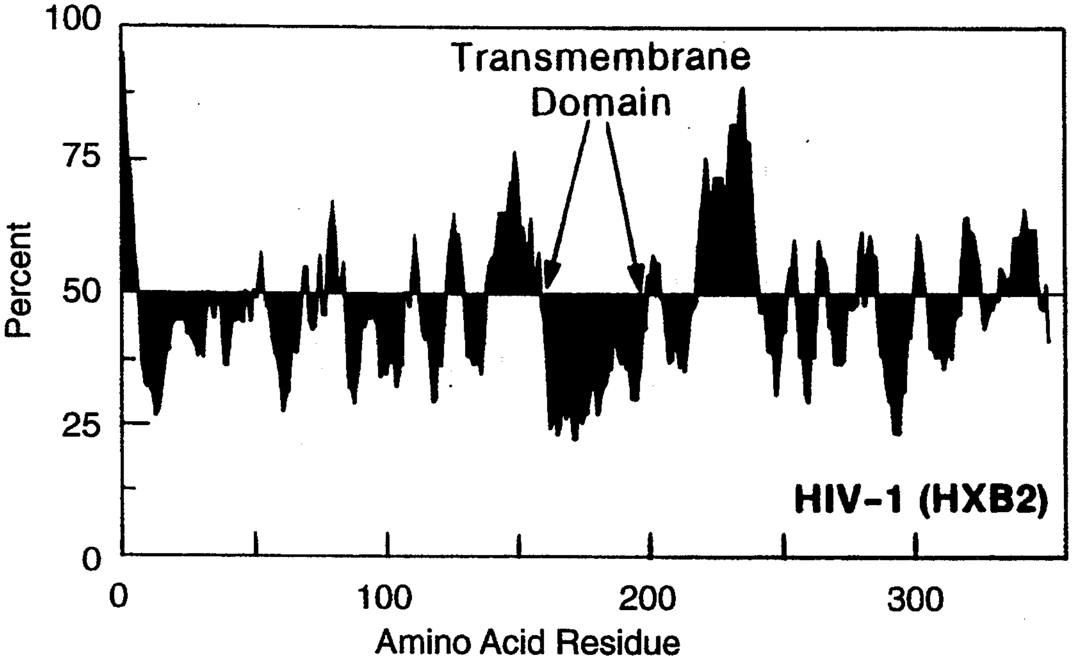

The OMP of BIV 127 and HIV-1 are identical at about 13% of their amino acids. This limited degree of relatedness is not unexpected considering the great amount of genetic variability which exists between different HIV-1 isolates where the preponderance of variability falls within the OMP (Alizon et al, 1986, *Cell* 46:63–74; Starcich et al, 1986, *Cell* 45:637–648) and the limited identity (39%) observed between HIV-1 and HIV-2 OMPs (Guyader et al, Supra). Using the OMP/TMP cleavage site as the benchmark with which to align the env precursors of lentiviruses has proven to be a useful means for Identifying the TMPs of retroviruses (Braun et al, supra). A similar strategy was used to look for the TMP of BIV by making structural comparisons between BIV and HIV-1. The TMPs of lentiviruses have extracellular, transmembrane, and intracellular domains. FIG. 11A shows the alignment of the exterior and transmembrane domains of the BIV and HIV-1 TMPs, as determined by amino acid similarity and hydropathy plots. Overall, the homology is 25% for this TMP segment; but is much more limited in the intracellular domain (data not shown). Nevertheless, the hydropathy plots of the two TMPs FIG. 11B and 11C show a striking resemblance. Moreover, there are several cysteine residues conserved between BIV and HIV (FIG. 11A), as has been seen in other HIV-lentivirus comparisons (Braun et al, supra; Kawakami et al, supra).

Central region ORFs

The central regions of lentiviruses, especially those of the primate lentiviruses, are quite complex as they contain numerous nonstructural/regulatory genes (Haseltine, 1988, *J. Acquired Immune Def. Syn.* 1:217–240). In HIV-1 and HIV-2, at least six different ORFs (vif, tat, rev, X, U, and R) that are actively transcribed and translated have been identified (Haseltine, supra; Henderson et al, 1988, *Science* 241:199–201; Strebel et al, 1988, *Science* 241:1221–1223; Wong-Staal et al, 1987, *AIDS Res. Hum. Retroviruses* 3:33–39; Niederman et al, 1989, *Proc. Natl. Acad. Sci. USA* 86:1128–1132). X is found only in HIV-2 and simian lentiviruses and U is found only in HIV-1. A uniform nomenclature for the ORFs of the central region has been proposed (Gallo et al, 1988, *Nature* 333:504; Laurence, J., 1988, *AIDS res. Hum. Retroviruses* 4:vii–viii); we follow that nomenclature here with BIV, where structural analogy or sequence similarity exist.

BIV has five short ORFs in this region that contain a potential translation initiation signal. The first is derived from sequences in the central region and overlaps the 3′ end of pol at its amino terminus (nt 4601–5194). Its position and size are similar to those of the gene encoding the viral infectivity factor (vif) described for HIV-1, HIV-2, SIVs, and visna virus (Braun et al, supra; Chakrabarti et al, supra; Fukasawa et al, supra; Guyader et al, supra; Rather et al, supra). There is little amino acid homology to the vif ORFs of other lentiviruses; however, there is reasonably good conservation in hydropathy plots (data not shown).

The second short ORF initiates in the central region and overlaps the 5′ end of the large env ORF (nt 5228–5536), in frame with the ORF we have identified as vif. The translation of this ORF also contains a Cys-rich region found in nucleic acid binding proteins and the transactivator (tat) proteins of most lentiviruses (FIG. 12) (Braun et al, supra; Chakrabarti et al, supra; Guyader et al, supra; Kawakami et al, supra; Rather et al, supra). This Cys-rich region in BIV127 shares 56% amino acid identity (no gaps) with HIV-1; identity is significantly lower when the rest of the translation of this ORF is evaluated. In addition, residues downstream of the Cys motif are very basic, consistent with the structure of a nucleic acid binding protein. These two features and the location of this ORF are evidence that it represents a BIV tat ORF.

The tat genes of primate lentiviruses consist of two coding exons. The first is contained in the central region and the second in the 3′ end of env, but in a different reading frame from that of env and rev exon 2. The second tat exon is not considered necessary for function (Haseltine, supra). The first tat exon is larger than the second. The mature tat message is derived from the primary transcript by a complex splicing mechanism (Haseltine, supra). We searched for a second tat exon in BIV 127 in the translation of all three reading frames of the 3′ end of the BIV 127 env and found some amino acid homology for a small ORF (nt 7657–7782) in reading frame 1 of the translation (FIG. 6N) with the translation of the HIV-2 second tat exon (Guyader et al, supra):

```
BIV 127   . . . TNISRRRRRTGTQSQKAPRREETRLLEVSTRI G
                  || |      || ||         |     | |  |
HIV-2           KS ISTR . . . TG . DSQPTKKQKKTVEATVETDTGPGR
```

There is an additional transactivating protein/regulator of viral gene expression found in primate lentivirus genomes called rev [Haseltine, supra; Sodroski et al, 1986, *Nature* (London) 321:412–417]. It, like tat, is made up of two exons that are spliced into the mature mRNA from a primary transcript. The first rev coding exon is usually located near the 3′ end of the central region often overlapping the 5′ end of env; the second exon is found in the 3′ end of env, overlapping, but in a different reading frame from that of the TMP. The first exon of rev is usually smaller than the second exon. The rev protein is also a nucleic acid binding protein that contains stretches of basic amino acids highly enriched for Lys+Arg residues as has been seen in the rev of HIV-1 (Ratner et al, supra; Sodroski et al, supra) and in the hinge domain of nucleic acid binding proteins (Adler et al, 1988, *Cell* 52:685–695). The rev gene of visna virus, like that of the primate lentiviruses, is also transcribed as a large RNA precursor that is processed into mature form by multiple splicing (Davis et al, 1987, *J. Virol.* 61:1325–1331; Mazarin et al, 1988, *J. Virol.* 62:4813–4818). Thus, the rev gene of visna virus has two exons that contain Arg+Lys-rich regions, without the characteristic Cys-rich motif seen in tat. The visna virus rev exon 1 has been localized to the 5′ end of the env gene and in frame with it; rev exon 2 overlaps the TMP coding sequences, but is in a different reading frame (Mazarin et al, 1988).

There were no obvious small ORFs in, or overlapping, the 3′ end of the central region of BIV that appeared to be good candidates for the first rev exon of BIV. However, a potential ORF reminiscent of the second rev exon of visna virus was identified in the 3′ end of the BIV genome (nt 7571–8068) and in a different reading frame than that of env. It also is rich in Arg+Lys residues. These sequences probably represent BIV rev exon 2. The presence of the visna virus rev exon 1 in the env ORF prompted us to scan the analogous region in BIV for sequences that could represent rev exon 1. In the translation of the first 39 nt (nt 5415–5452) of the env ORF, there is some amino acid homology to rev exon 1 of HIV-2 (Guyader et al, 1987). The sequence for this 39 amino acid stretch begins Met-Asp-Gln-Asp-Leu and precedes the predicted hydrophobic leader sequence for env as in visna virus (Mazarin, supra; Gonda, supra). This rev exon is preceded by a potential splice acceptor site (nt 5396) and followed by a splice donor site (nt 5452), which would put these sequences in frame with those proposed for the BIV rev exon 2, when using a splice acceptor site at nt 7648. The predicted size for the product of this gene is 17 kd (153 aa) (Table 2), which is about the same size as the 18 kd (167 aa) rev gene product of visna virus, predicted from the translation of a eDNA clone (Mazarine et al, supra).

There are two additional short ORFs in the BIV central region that contain a potential AUG start site. These two unique ORFs have been designated herein as W (nt 4729–4890) and Y (nt 5089–5328). The predicted products for the W and Y ORFs are 54 and 80 amino acids, respectively. ORF W contains a strong consensus signal sequence for the initiation of translation at the first AUG in this ORF, while that of Y is weak (Kozak, 1986, *Cell* 44, 283–191; Kozak, 1989, *J. Cell Biol.* 108, 229–241). In addition, there is a potential splice acceptor site immediately upstream of both ORF W and Y. The presence of a strong consensus signal sequence in W suggests that this ORF may be actively translated, possibly from a spliced message. The fate of X is more speculative. Interestingly, W and X are located in positions in the central region analogous to vpr, vpu, or vpx encoding ORFs of HIV-1 or HIV-2, respectively. No amino acid or nucleotide similarities for BIV ORFs W and Y were found with ORFs of the central region of primate or ruminant lentiviruses. However, it was noted that Y appears to have a significant number of basic amino acids and thus, based on this property, appears to bear some resemblance to a nucleic acid-binding protein.

Genomic variability in the BIV 106 and 127 molecular clones

The genomes of lentiviruses are known to be highly variable. The sequencing of the two functional proviral clones of BIV presented the opportunity to examine the amount and location of diversity between them. There were 137 nucleotide changes (Table 1); 91 of these were deletions in BIV 106 and 87 of these occurred at a single site in the envelope. The BIV 106 $U_3$, R, and $U_5$ elements (FIG. 8) had 8 nucleotide changes and 4 of these were deletions. There were no deletions in BIV 127 relative to BIV 106. Of the 46 nucleotide substitutions, 42 are in putative structural or nonstructural/regulatory genes and are responsible for 24 coding substitutions. Several substitutions caused coding changes in overlapping ORFs. Most of the predicted replacements are relatively conservative; 6, however, result in charge changes.

Figure 13A:
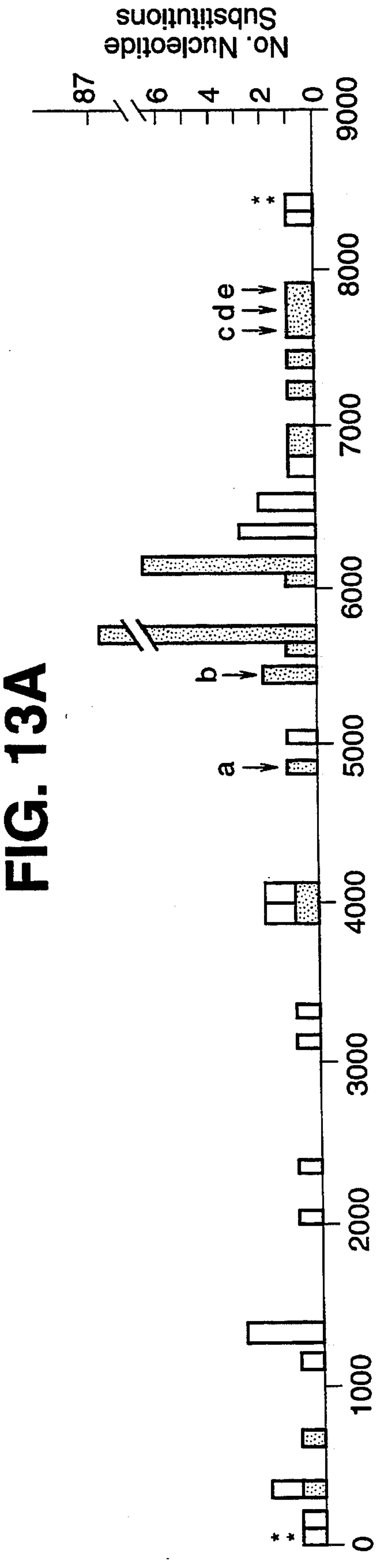
FIG. 13A shows the distribution of nucleotide substitutions between BIV 106 and 127. The positions of the major open reading frames are shown in FIG. 13B. The arrow over the env segment in FIG. 13B represents the OMP/TMP cleavage site. Each box in FIG. 13A represents one substitution and substitutions are cumulatively displayed every 100 nt Designations a–e in FIG. 13A indicate the following: a) Coding substitutions in both W and vif. b) Two nucleotide substitutions which cause coding changes in tat exon 1, but only one of the two causes a coding change in env. c) Coding changes in env and rev exon 2, but not tat exon 2. d) Nucleotide substitution which causes coding changes in rev exon 2 and tat exon 2, but not in env. e) Nucleotide substitution which causes a coding change in rev exon 2, but not in env.
Figure 13B:
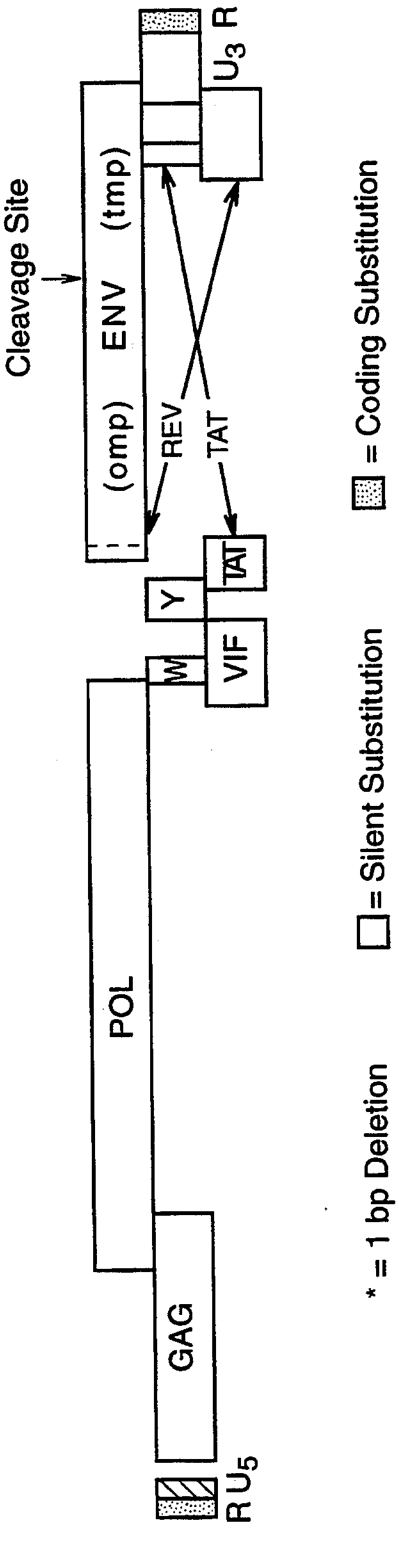

FIGS. 13A and 13B shows diagrammatically the distribution of nucleotide substitutions between BIV clones 106 and 127; the substitutions were graphed cumulatively for each 100 nt segment. In the structural genes, there were 7 substitutions in gag, 8 in pol, and 24 (111 counting the major deletion) in env (19 in OMP; 5 in TMP). In the nonstructural/regulatory genes, vif had 2, tat exon 1 had 2, tat exon 2 had 2, rev exon 2 had 3, and W had 1 substitution(s). By visual analysis of FIGS. 13A and 13B a non-random distribution of substitutions is observed even when the major deletion in env is ignored. For the structural genes, the graph indicates that there are a larger number of substitutions in env and that there are local regions of greater variability within env. Analysis of substitutions indicates that the env gene contains the greatest number of coding substitutions (gag=2 of 7; pol=2 of 8; and env=12 of 24). In addition, within env, OMP has the highest number of substitutions, suggesting that the OMP is the most variable region of the genome. For the structural genes gag, pol, and env, $X^2$ analysis was used to test whether the number of observed nucleotide changes In the env gene, and in particular the OMP region, exceeded what would be expected if the changes (excluding the 87 nt deletion) were random over the lengths of each functional unit (gag, pol, OMP, and TMP). The results ($p=0.0003$) of this $X^2$ analysis statistically support the conclusion that the OMP of the env gene is the most variable segment of the BIV genomes used in the comparison.

In summary, two distinct molecular clones of functional BIV proviruses have been obtained and their complete nucleotide sequence determined. Upon microinjection into susceptible cells, these clones mimic the biological activity of BIV virus stocks, including the induction of syncytia, reverse transcriptase activity, virus particle formation, and cell-free transmission. These two clones (106 and 127) are independent isolates in that the proviruses are flanked by different cellular sequences, as shown by heteroduplex mapping. Although the two proviruses themselves are highly related, they differ in cytopathogenicity.

The availability of the biologically active proviral molecular clones, stable cell lines infected by them, the determination of the complete nucleotide sequence of these clones and the proteins synthesized by them, now makes it possible to employ these clones or specific segments thereof as reagents for making antigens, antibodies and DNA probes for diagnostic tests for BIV. Of course, the clones, or antigenic products made therefrom, can be used to prepare anti-BIV vaccines. Moreover, these unique functional clones of BIV with complete nucleotide sequences allow for the first time to dissect the molecular mechanisms of pathogenesis of BIV which may provide a model for the study of other lentiviruses such as HIV.

A diagnostic kit for the detection of BIV in accordance with the present invention, comprises a container containing BIV-specific DNA which is then employed to detect BIV through standard hybridization techniques well known in the art.

Stable cell lines infected with the BIV also allow for the first time to prepare substantially pure (as pure as possible to achieve by conventional isolation and purification techniques) BIV stocks from which to obtain substantially pure BIV-proteins, DNA and the like. Conventional isolation and purification techniques can be found described in any standard virology or molecular biology text books, laboratory manuals and the like.

ATCC Deposits.

A deposit of the following clones and cell lines have been made at the ATCC, Rockville, Md. on Sep. 15, 1989.

| Clone/Cell Line | ATCC No. |
|---|---|
| pBIV106(inf) | 68093 |
| pBIV127(inf) | 68092 |
| BIV106/EREp | CRL 10227 |
| BIV127/EREp | CRL 10228 |

These deposits shall be viably maintained, replacing if it becomes non-viable during the life of the patent, for a period of 30 years from the date of the deposit, or for 5 years from the last date of request for a sample of the deposit, whichever is longer and upon issuance of the patent made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Nucleotide sequence differences between BIV strain 127 and 106.

| Functional unit | Nucleotide position | Base in strain: 127 | 106 | Amino acid in strain: 127 | 106 |
|---|---|---|---|---|---|
| R-$U_5$ | 48 | G | A | NC | NC[1] |
| | 99 | T | — | NC | NC |
| | 100 | T | — | NC | NC |
| | 167 | T | G | NC | NC |
| gag | 327 | G | A | Arg | Arg |
| | 365 | C | T | Pro | Leu |
| | 666 | T | A | Asp | Glu |
| | 1176 | C | A | Pro | Pro |
| | 1338 | T | C | Pro | Pro |
| | 1350 | C | T | Asn | Asn |
| | 1395 | T | C | Ser | Ser |
| pol | 2036 | C | A | Thr | Thr |
| | 2390 | T | C | Thr | Thr |
| | 3140 | G | A | Glu | Glu |
| | 3305 | A | T | Pro | Pro |
| | 3989 | T | G | Pro | Pro |
| | 3991 | A | G | Lys | Arg |
| | 4031 | T | C | Cys | Cys |
| | 4044 | A | G | Thr | Ala |
| vif | 4850 | G | A | Asp | Asn |
| | 5029 | G | A | Leu | Leu |
| W | 4850 | G | A | Arg | Lys |
| tat (exon 1) | 5408 | A | G | Ile | Val |
| | 5484 | G | A | Gly | Glu |
| env (OMP) | 5484 | G | A | Glu | Lys |

TABLE 1-continued

Nucleotide sequence differences between BIV strain 127 and 106.

| Functional unit | Nucleotide position | Base in strain: 127 | Base in strain: 106 | Amino acid in strain: 127 | Amino acid in strain: 106 |
|---|---|---|---|---|---|
| | 5688 | G | A | Glu | Lys |
| | 5819–5905[2] | 87 nt | — | 29aa | — |
| | 6060 | G | A | Val | Ile |
| | 6120, 6121 | A, G | C, T | Ser | Leu |
| | 6156, 6158 | T, G | C, A | Trp | Arg |
| | 6178 | A | G | Asn | Ser |
| | 6192 | A | G | Met | Val |
| | 6236 | T | C | Asn | Asn |
| | 6263 | A | G | Val | Val |
| | 6443 | T | C | His | His |
| | 6455 | A | G | Thr | Thr |
| | 6473 | A | G | Leu | Leu |
| | 6518 | C | T | Asp | Asp |
| | 6560 | C | T | Ser | Ser |
| | 6782 | A | G | Gln | Gln |
| | 6894 | T | C | Phe | Leu |
| | 6976 | A | G | Lys | Arg |
| env (TMP) | 7285 | A | G | His | Arg |
| | 7429 | A | G | Asn | Ser |
| | 7698 | G | A | Ala | Thr |
| | 7724 | G | A | Glu | Glu |
| | 7877 | T | C | Asp | Asp |
| rev (exon 2) | 7698 | G | A | Gly | Asp |
| | 7724 | G | A | Ala | Thr |
| | 7877 | T | C | Ser | Pro |
| tat (exon 2) | 7698 | G | A | Arg | Arg |
| | 7724 | G | A | Ser | Asn |
| $U_3$-R | 8344 | A | G | NC | NC |
| | 8419 | G | A | NC | NC |
| | 8470 | T | — | NC | NC |
| | 8471 | T | — | NC | NC |

[1]NC = No change.

[2]This represents the 87 bp deletion (29aa) in BIV106 relative to BIV127 (see FIGS. 6A–6D).

TABLE 2

Putative Protein Products of BIV 127 ORFs.

| ORF | HIV-1 Equivalent | Position | MW (daltons) |
|---|---|---|---|
| gag[1] | gag precursor (p55) | nt316–1743 | 53440 |
| | $p16^{gag}$ | aa1–148 | 17070 |
| | $p25^{gag}$ | 149–351 | 22803 |
| | $p15^{gag}$ | 352–476 | 13602 |
| pol[2] | pol precursor | nt1581–4739 | 120658 |
| | protease | aa51–143 | 10564 |
| | reverse transcriptase | 144–774 | 72157 |
| | endonuclease | 775–1053 | 32054 |
| env[3] | env precursor | nt5415–8126 | 102269 |
| | OMP | aa1–555 | 62098 |
| | TMP | 556–904 | 40189 |
| vif | vif | 4601–5194 | 22828 |
| W | ? | 4729–4890 | 6620 |
| Y | ? | 5089–5328 | 9549 |
| tat exon 1 | tat exon 1 | 5228–5536 | 11689[4] |
| tat exon 2 | tat exon 2 | 7657–7782 | ND[5] |
| rev exon 1 | rev exon 1 | 5415–5452 | ND[5] |
| rev exon 2 | rev exon 2 | 7571–8068 | 17098[6] |

[1]Alignment of BIV 127 gag and $HIV\text{-}1_{HXB2}$ gag by PIR Align program using a gap penalty of 6 and 300 random runs (Needleman and Wunsch, 1970). Processing products were derived from comparison with $HIV\text{-}1_{HXB2}$ (Mervis et al., 1988).

[2]Alignment of BIV 127 pol and $HIV\text{-}1_{HXB2}$ pol by PIR Align and UWGCG Gap programs. Protease-RT junction interred from BIV-$HIV\text{-}1_{HXB2}$ comparison (Lillehoj et al., 1988); endonuclease homology from BIV-visna virus and visna virus-HIV comparisons (Braun et al., 1987).

[3]Alignment of BIV 127 env and $HIV\text{-}1_{HXB2}$ env by PIR Align program. Processing products from comparison of BIV and $HIV\text{-}1_{HXB2}$ (Muesing et al., 1985).

[4]Molecular weights for tat exons 1 and 2 translated from a predicted spliced message.

[5]ND = Not determined.

[6]Molecular weights for rev exons 1 and 2 translated from a predicted spliced message.

What is claimed is:

1. Isolated and purified BIV proviral DNA with the nucleotide sequence as shown in FIGS. 6A–6D.

2. An isolated and purified, infectious, proviral molecular clone of BIV which is clone BIV106.

3. An isolated and purified, infectious, proviral molecular clone of BIV which is clone BIV127.

* * * * *